US006265563B1

(12) United States Patent
Evans et al.

(10) Patent No.: US 6,265,563 B1
(45) Date of Patent: Jul. 24, 2001

(54) OPIOID RECEPTOR GENES

(75) Inventors: Christopher J. Evans, Venice; Duane E. Keith, Woodland Hills; Robert H. Edwards, Los Angeles; Daniel Kaufman, Santa Monica, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/387,707

(22) Filed: Feb. 13, 1995

Related U.S. Application Data

(63) Continuation-in-part of application No. 07/929,200, filed on Aug. 13, 1992, now abandoned.

(51) Int. Cl.$^7$ .......................... C07H 21/04; C12P 21/06; C12P 21/04; C12N 1/20
(52) U.S. Cl. ...................... 536/23.5; 435/70.1; 435/71.1; 435/71.2; 435/252.3; 435/320.1; 435/325; 435/240.2; 435/254.11; 435/475; 435/69.1
(58) Field of Search ............................... 435/69.1, 320.1, 435/240.2, 252.3, 254.11, 70.1, 71.1, 71.2, 325, 471; 536/23.5

(56) References Cited

PUBLICATIONS

Libert et al (1989) Science 244: 569–572.*
Akiyama et al., *Proc. Natl. Aci. USA*, pp. 2543–2547 (1985).
Bochet et al., *Molecular Pharmacology*, vol. 34, pp. 436–443 (1988).
Carr et al., *Immunology Letters*, vol. 20, No. 3, pp. 181–186 (1989).
Davis et al., "Basic Methods in Molecular Biology," Elsevier Science Publishing Co., Inc., New York, pp. 1–372 (Table of Contents provided), (1986).
Eberwine et al., *Federation Proceedings*, vol. 46, No. 4, p. 1444, abstract No. 6582 (1987).
Erspamer et al., *Proc. Natl. Acad. Sci. USA*, vol. 86, pp. 5188–5192 (1989).
Evans et al., *Society for Neuroscience Abstracts*, vol. 18, Part 1, p. 21, abstract 16.1 (1992).
Evans et al., *Science*, vol. 258, pp. 1952–1955 (1992).
Evans, C. J. In: *Biological Basis of Substance Abuse*, S.G. Korenman & J.D. Barchas, eds., Oxford University Press (1993).
Garcel et al., *FEBS Letters*, vol. 118, pp. 245–247 (1980).
Gilbert et al., *J. Pharmacol. Exp. Ther.*, vol. 198, pp. 66–82 (1976).
Goodman and Gilman's *The Pharmacological Basis of Therapeutics*, 7th ed., pp. 493–495 (MacMillan 1985).
Gross et al., *Proc. Natl. Acad. Sci. USA*, vol. 87, pp. 7025–7029 (1990).
Kieffer et al., *Proc. Natl. Acad. Sci. USA*, 89, pp. 12048–12052 (1992).

Klee et al., *Proc. Natl. Acad. Sci. USA*, vol. 71, pp. 3474–3477 (1974).
Langord et al., *Biochem. Biophys. Res. Comm.*, vol. 138, pp. 1025–1032 (1992).
Law et al., *Molecular Pharmacology*, vol. 21, pp. 438–491 (1982).
Lord et al., *Nature*, vol. 267, pp. 495–499 (1977).
Louie et al., *Biochem. Biophys. Res. Comm.*, vol. 152, pp. 1369–1375 (1988).
Mansour et al., *Trends in Neurosci.*, vol. 11, pp. 308–314 (1988).
Mulder et al., *Eur. J. Pharmacol.*, vol. 205, pp. 1–6 (1991).
Negri et al., *Eur. J. Pharmacol.*, vol. 196, pp. 335–336 (1991).
Pert et al., *Science*, vol. 179, pp. 1011–1014 (1973).
Sanger et al., *Proc. Natl. Acad. Sci. USA*, vol. 74, No. 12, pp. 5463–5467 (1977).
Schofield et al., *The EMBO Journal*, vol. 8(2), pp. 489–495 (1989).
Sharma et al., *Proc. Natl. Acad. Sci. USA*, vol. 72, pp. 3092–3096 (1975).
Sofuoglu et al., *The Pharmacologist*, vol. 32, p. 151 (1990) Abstract No. 51/185.
Strosberg, A.D., *Eur. J. Biochem.*, vol. 196, pp. 1–10, Abstract No. 185 (1991).
Takemori et al., *Ann. Rev. Pharm. Toxicol.*, vol. 32, pp. 239–269 (1992).
Terenius, L., *Eur. J. Pharmacol.*, vol. 38, p. 211 (1976).
Tsunoo et al., *Proc. Natl. Acad. Sci. USA*, vol. 83, pp. 9832–9836 (1986).
Wollemann, M., *J. Neurochem.*, vol. 54, pp. 1095–1101 (1990).
Xie et al., *Proc. Natl. Acad. Sci. USA*, vol. 89, pp. 4124–4128 (1992).
Yasuda et al., *Proc. Natl. Acad. Sci. USA*, vol. 90, pp. 6736–6740 (1993).
Yu et al., *J. of Biol. Chem.*, vol. 261, No. 3, pp. 1065–1070 (1986).
Gramsch et al., "Monoclonal Anti–idiotypic Antibodies to Opioid Receptors," *Jour of Biological Chem*, vol. 263, No. 12, pp. 5853–5859 (1988).
Machida et al., "Three Technical Approaches for Cloning Opioid Receptors," *Natl Institute on Drug Abuse Research Monograph Series*, pp. 93–110, (1988).

(List continued on next page.)

Primary Examiner—Gary L. Kunz
Assistant Examiner—Robert S. Landsman
(74) Attorney, Agent, or Firm—Morrison & Foerster LLP

(57) ABSTRACT

Genes encoding opioid receptors can be retrieved from vertebrate libraries using the murine probe disclosed herein under low-stringency conditions. The DNA sequence shown in FIG. 5 or its complement can be used to obtain the human delta, kappa and mu genes as well as the murine mu gene. The probe provided encodes the murine delta opioid receptor.

10 Claims, 21 Drawing Sheets

OTHER PUBLICATIONS

Simonds et al., "Purification of the opiate receptor of NG108–15 neuroblastoma–glioma hybrid cells," *Proc. Natl. Acad. Sci.*, vol. 82, pp. 4974–4978 (1985).

Smith et al., "Problems and Approaches in Studying Membrane Opioid Receptors," *Natl Institute on Drug Abuse Research Monograph Series*, pp. 69–84, (1991).

* cited by examiner

```
GCACGGTGGAGACGGACACGGGCGGCCATG GAG CTG GTG CCC TCT GCC CGT GCG GAG CTG CAG TCC CCC CTC
                               Met Glu Leu Val Pro Ser Ala Arg Ala Glu Leu Gln Ser Pro Leu

GTC AAC CTC TCG GAC GCC TTT CCC AGC GCC TTC CCC AGC GGC GCC AAT GCG TCG GGG TCG CCG GGA
Val Asn*Leu Ser Asp Ala Phe Pro Ser Ala Phe Pro Ser Gly Ala Asn*Ala Ser Gly Ser Pro Gly

GCC CGT AGT GCC TCG TCC CTC GCC CTA GCC ATC GCC ACC GCG CTC TAC TCG GCT GTG TGC GCA GTG
Ala Arg Ser Ala Ser Ser Leu Ala Leu Ala Ile Ala Thr Ala Leu Tyr Ser Ala Val Cys Ala Val

GGG CTT CTG GGC AAC GTG CTC ATG TTT GGC TAC ATC GTC ACC TAC ACC AAA TTG AAG ACC GCC AAC
Gly Leu Leu Gly Asn Val Leu Met Phe Gly Ile Val Arg Tyr Thr Lys Thr Leu Lys Thr Ala Asn

ATC TAC ATC TTC AAT CTG GCT TTG GCT GAT GCG GCA CTG GCC ACC CTG CCC CTT CAG AGC GCC AAG
Ile Tyr Ile Phe Asn Leu Ala Leu Ala Asp Ala Ala Leu Ala Thr Leu Pro Phe Gln Ser Ala Lys

TAC TTG ATG GAA ACG TGG CCG TTT GGC GAG CTG CTG TGC AAG GCT GTG CTC TCC ATT GAC TAC TAC AAC
Tyr Leu Met Glu Thr Trp Pro Phe Gly Glu Leu Leu Cys Lys Ala Val Leu Ser Ile Asp Tyr Tyr Asn

ATG TTC ACT AGC ATC TTC CTC ATG ACC ATG AGC AGC CGC CGC TAC ATT GCT GTC TGC CAT CCT GTC
Met Phe Thr Ser Ile Phe Leu Met Thr Met Ser Ser Arg Arg Tyr Ile Ala Val Cys His Pro Val

AAA GCC CTG GAC TTC CGG ACA CCA GCC AAG GCC AAA CTG AAT ATA TGC ATC TGG GTC TTG GCT TCA
Lys Ala Leu Asp Phe Arg Thr Pro Ala Lys Ala Lys Leu Asn Ile Cys Ile Trp Val Leu Ala Ser

GGT GTC GGG GTC CCC ATC ATG GTC ATG GCA GTG CAA CCC CGG GAT GGT GCA GTG TGC GTA TGC ATG CTC
Gly Val Gly Val Pro Ile Met Val Met Ala Val Gln Pro Arg Asp Gly Ala Val Cys Val Cys Met Leu
```

FIG.5a

CAG TTC CCC AGT CCC AGC TGG TAC TGG GAC ACT GTG ACC AAG ATC TGC GTG TTC CTC TTT GCC TTC GTG
Gln Phe Pro Ser Pro Ser Trp Tyr Trp Asp Thr Val Thr Lys Ile Cys Val Phe Leu Phe Ala Phe Val

GTG CCG ATC CTC ATC ATC ACG GTG TGC TAT GGC CTC ATG CTA CTG CGC AGC GTG CGT CTG CTG
Val Pro Ile Leu Ile Ile Thr Val Cys Tyr Gly Leu Met Leu Leu Arg Ser Val Arg Leu Leu

TCC GGT TCC AAG GAG AAG GAC CGG AGC CTG CGG CGC ATC ACG CGC ATG GTG CTG GTG GTG GGC GCC
Ser Gly Ser Lys Glu Lys Asp Arg Ser Leu Arg Arg Ile Thr Arg Met Val Leu Val Val Gly Ala

TTC GTG GTG TGC TGG GCG CCC ATC CAC ATC TTC GTC ATC GTG TGG ACG CTG GTG GAC ATC AAT CGG CGC
Phe Val Val Cys Trp Ala Pro Ile His Ile Phe Val Ile Val Trp Thr Leu Val Asp Ile Asn Arg Arg

GAC CCA CTT GTG GTG GCC GCA CTG CAC CTG TGC ATT GCG CTG GGC TAC GCC AAC AGC CTC AAC CCG
Asp Pro Leu Val Val Ala Ala Leu His Leu Cys Ile Ala Leu Gly Tyr Ala Asn Ser Leu Asn Pro

GTT CTC TAC GCC TTC CTG GAC GAG AAC TTC AAG CGC TGC TTC CGC CAG CTC TGT CGC ACG TGC GGC
Val Leu Tyr Ala Phe Leu Asp Glu Asn Phe Lys Arg Cys Phe Arg Gln Leu Cys Arg Thr Cys Gly

CGC CAA GAA CCC GGC AGT CTC CGT CCC CGC CAG GCC ACG ACG GAG CGT GTC ACT GCC TGC ACC
Arg Gln Glu Pro Gly Ser Leu Arg Pro Arg Gln Ala Thr Thr Arg Glu Arg Val Thr Ala Cys Thr

CCC TCC GAC GGC CCG GGT GGC GCT GCC GCC TGA CCTACCCGACCTTCCCCTTAAACGCCCCTCCCAAGTGAAGTGA
Pro Ser Asp Gly Pro Gly Gly Gly Ala Ala Ala ***

CAGAGGCCACACCGAGCTCCCTGGGAGGCTGTGTGGCCACCAGGACAGCAGCAGGAGAGGGAGGCCTCCTGTGGGGAC
GGCCTGAGGGATCAAAGGCTCCAGGTTGAGATAACATCTGGTGATTCCATTCCTAAGAGCTGGTGATCCAATTAGTAAGGCCTCT
AATGGGACAGAGGGGCCGCTCCGCTTGAGATGGCTCCAGCTTGAACACCCAGCTCCAAGAGACCCAAGGATCTCTCAGCTCCA
AACCAGGAGGAGGGCAGTGATGATCAGGCAAGGCATTTGGTTTGGCTGAGAGTCCAGGAGATAAGCGCCCCCTTGAGGGAAGAAG
AAGGGAGACAGGGGCCAGGAGAGAAGTCAAAGTTCTACACCTTTCTAACTACTCAGCCTAAACTCGTTGAGGCTAGGCTGACTTCTCTGAGGATGGT
ACGTTGGAGAGCCGGGCCTGATGGGCCAGGCAGGCTGTGTAATCCCAGTCATAGTGGAGGCTGGAAAATTAAGGACCAACAGCCCGG
TACAAGCCGCGGCCTGATGGGCCAGGCAGGCTGTGTAATCCCAGTCATAGTGGAGGCTGGAAAATTAAGGACCAACAGCCCGG

FIG. 5b

```
            *20                   *              40
MELVPSARAELQSSPLVNLSDAFPSAFPSAGANASGSPGARSAS--SLALAIAITALYSA
                 : ::  :   ::::  : :  : :: :   ::::: :::::
            MELTSEQFNGSQVWIPSPFDLNGSLGPSNGSNQTEPYYDMTSNAVLTFIYFV 60                80                 100
VCAVGLLGNVLVMFGIVRYTKLKTATNIYIFNLALADALATSTLPFQSAKYLMETWPFGE
:: ::::: :: :::::::::  :::::::: ::: :::  ::: :  :::: :::::
VCVVGLCGNTLVIYVILRYAKMKTITNIYILNLAIIADELFMLGLPFLAMQVALVHWPFGK 120              140                160
LLCKAVLSIDYYNMFTSIFTLTMMSVDRYIAVCHPVKALDFRTPAKAKLINICIWVLASG
:: :::: : ::: :::: :: :::::::::::::::::::::::::: :: :::::::
AICRVVMTVDGINQFTSIFCLTVMSIDRYLAVVHPIKSAKWRRPRTAKMINVAVWGVSLI 180             200              220
VGVPIMVMAVTQPRD-GAVVCMLQFPSPSWYWDTVTKICVFLFAFVVPILIITVCYGLML
: : ::: : :: : : :::: :: : :: : :::  :: : ::: :: : :: :: :
VILPIMIYAGLRSNQWGRSSCTINWPGESGAWYTGFIIYAFILGFLVPLTIICLCYLFII 240              260               280
LRLRSVRLLSGSKEKDRSLRRITRMVLVVVGAFVVCWAPIHIFVIVWTLVDINRRDPLVV
:: :: :  :: : :::: ::::::: : ::: : :::: ::: : :: ::   :: :
IKVKSSGIRVGSSKRKKSEKKVTRMVSIVVAVFIFCWLPFYIFNVSSVSVAIS-PTPALK 300               320                340
AALHLCIALGYANSSLNPVLYAFLDENFKRCFRQ-LCRTPCGRQEPGSLRRPRQATTRER
 :  ::: :::::: :::::::::::: : :::  :::  ::::: :::::::::::::
GMFDFVVILTYANSCANPILYAFLSDNFKKSFQNVLCLVKVSGAEDGERSDSKQDKSRLN 360       370
VTACTPSDGPGGGAAA

ETTETQRTLLNGDLQTSI
```

FIG.6

HUMAN DELTA

```
Sequence Range: -131 to -1
                 -122*      -112*      -102*      -92*       -82*
Tuyet's H3  -GG GCA GTG TGC ATG CTC CAG TTC CCC AGC CCC AGC TGG TAC TGG GAC ACG
             610         620         630         640         650         660
DOR-1       gGt GCA GTg TGC ATg CTC CAG TTC CCc AGt CCC AGC TGG TAC TGG GAC ACt
[ 478 ]     ^^^ ^^^ ^^a ^^^ ^^^ ^^^ ^^^ ^^^ ^^^ ^^v ^^^ ^^^ ^^^ ^^^ ^^^ ^^^ ^^v -72*       -62*       -52*       -42*       -32*
Tuyet's H3  GTG ACC AAG ATC TGC GTG TTC CTC TTC GCC TTC GTG GTG CCC ATC CTC ATC ATC
                         670         680         690         700         710
DOR-1       GTG ACC AAG ATC TGC GTG TTC CTC TTt GCC TTC GTG GTG CCg ATC CTC ATC ATC
            ^^^ ^^^ ^^^ ^^^ ^^^ ^^^ ^^^ ^^^ ^^t ^^^ ^^^ ^^^ ^^^ ^^v ^^^ ^^^ ^^^ ^^^

-22*       -12*       -2*
Tuyet's H3  ACC GTG TGC TAT GGC CTC ATG CT
             720         730
DOR-1       ACg GTG TGC TAT GGC CTC ATG C
            ^^v ^^^ ^^^ ^^^ ^^^ ^^^ ^^^ ^
```

FIG.8a

```
         10          20          30          40
          *           *           *           *
CCT GGC CTT TTG GGG ATG TGC TGT GCA AGA TAG TAA TTT CCA TTG
     50          60          70          80          90
      *           *           *           *           *
ATT ACT ACA ACA TGT TCA CCA GCA TCT TCA CCT TGA CCA TGA TGA
        100         110         120         130
          *           *           *           *
GCG TGG ACC GCT ACA TTG CCG TGT GCC ACC CCG TGA AGG CTT TGG
    140         150         160         170         180
      *           *           *           *           *
ACT TCC GCA CAC CCT TGA AGG CAA AGA TCA TCA ATA TCT GCA TCT
        190         200         210         220
          *           *           *           *
GGC TGC TGT CGT CAT CTG TTG GCA TCT CTG CAA TAG TCC TTG GAG
    230         240         250         260         270
      *           *           *           *           *
GCA CCA AAG TCA GGG AAG GTA AGA GCA GTC ATT TCA TTC TGT TCA
        280         290         300         310
          *           *           *           *
TAA AAA TGT AGC TTC AAA TTA CAT AGA CTT TTA ATT TGA GCG TGA
    320         330         340         350         360
      *           *           *           *           *
GTA GGC CAC ATA TTT GTG GAA ATC GAT GCC AAA AGA CGA CGG AAA
        370         380         390         400
          *           *           *           *
TGT AGT GCC TAA ATC CAT GGA AGA TGA GAA GTA GAA CAA TTT TTT
    410         420         430         440         450
      *           *           *           *           *
GTC CCT TTC CAC CTC TAA ACA CAG AAT GCA ATA ATG ACA TTG CCA
        460         470         480         490
          *           *           *           *
GAA GAG AGA TGC CCG ACC TGT CTC CCA TTC TGG CAA TGT TTA GTA
    500         510         520         530         540
      *           *           *           *           *
GAA AGT GGA GGG GTG AGG ATG AGG TAA GAA CCA CAG GCA TGT AGA
        550         560         570         580
          *           *           *           *
TTT TAA AGT ACA ACC TGG CAA GTC CAG ACA CAC CTT CTC ACT CCT
    590         600         610         620         630
      *           *           *           *           *
TTT TTT CTC TTT AAC AAG GGA TAT AAA TTA TTG GTG ACA TAT GCT
        640         650         660         670
          *           *           *           *
GGT TGT TTC CTC TTT TAT TCC TAA AGG ATA ACC TCC AAA TCA CTA
```

FIG.8b-1

```
       680         690         700         710         720
        *           *           *           *           *
TTT TAA CAG CTT TGG CGT AGG ATC TCA AAA TCA AGT TAA CGG ATG
           730         740         750         760
            *           *           *           *
GTA GTT ACA GAT GAG TCA GAA CCA CTT GAT TTG GAC ATA TCA GGT
  770         780         790         800         810
   *           *           *           *           *
TTT CCC TTG CAA ACC AGC CAA CTG ATT TTT TTT TTT TTT TTT TTT
           820         830         840         850
            *           *           *           *
GAG AGA GAG TCT TGC TCT GTT GCC AGG CTA GAG TGC AGT GGC GCG
  860         870         880         890         900
   *           *           *           *           *
ATA TCG GCT CAC TGC AAC CTC TGC CTC CCG GGT TCA ACC TCA GCC
           910         920         930         940
            *           *           *           *
TCT CGA GTA GCT GGG ACT ACT GGC ACA CAC CAC CAT GCC CAG CTA
  950         960         970         980         990
   *           *           *           *           *
ATT TTT GTA TTT TTA GTA GAG ACA GGG TTT CAC CGT GTT GGC CAG
           1000        1010        1020        1030
            *           *           *           *
GGT GGT CTC AAT CTC TTG ACC TCG TGA TCT GCC CGC CTC GNC TCC
  1040        1050        1060        1070        1080
   *           *           *           *           *
CCA AAG TGC TGG GAT TAC AGG CGT GCN CTG CNC CCG NCC CCT GTT
           1090        1100        1110        1120
            *           *           *           *
GAT GTT TTT CCT GTA TTT CTA GGA CAG TAG TTC TCA CTC TGG GCT
  1130        1140        1150        1160        1170
   *           *           *           *           *
GCA CAT TGG AAT CAC CTG GGT ACT TTA GAA AAC ACT GCT GCC TGC
           1180        1190        1200        1210
            *           *           *           *
ATC CCA CCC CTT AAG GGT CTG GTG TAA TTG ACC TGG GGT ACA GCC
  1220        1230        1240        1250        1260
   *           *           *           *           *
TGG GTG TCA AGA TTT TTG AGC TCT CTC CAG GTG ACT CTG ACC TGC
           1270        1280        1290        1300
            *           *           *           *
AGC CAA GGT GAG AGG TAC TGT TCT AGG AGT TTT GCT TTA CTA GCA
  1310        1320        1330        1340        1350
   *           *           *           *           *
AAA TAT AAA GCT ATA GAA AGC ATC TTT TGT TCC TCA TAG AAA TTA
```

FIG.8b-2

```
       1360         1370         1380         1390
        *            *            *            *
ATG ATG GGG AGG TGA GCA GAA TAG TCA CTC TGG GCC TAC TCA TGC
    1400         1410         1420         1430         1440
     *            *            *            *            *
TGT TTA ATG CTC CAG CAG GTA TAT AGG TTC TCC AGT TAC TAG GGG
       1450         1460         1470         1480
        *            *            *            *
GTT CAT AAT ACC TGT GAG AGC AGA TAA CTG AGT GTA TAT AGT GAG
    1490         1500         1510         1520         1530
     *            *            *            *            *
GAT TTC CAG GTC ATA GTG AAA GGG CAA GGC ACT AAA ATC ATA GCT
       1540         1550         1560         1570
        *            *            *            *
TGT CTT GCA TAT ACT GTT TGT TTG TTT TTA GAC TTA CAT GTT AGG
    1580         1590         1600         1610         1620
     *            *            *            *            *
TTT CAG TTT ACG TTT TAG GTT CAC AGC AAA ACT GAC CAG AAA GCA
       1630         1640         1650         1660
        *            *            *            *
CAG AGA GGC ACT TCN ATT TAC CTC CAT TTA CCC CAC ACA GGC ACA
    1670         1680         1690         1700         1710
     *            *            *            *            *
TCC TCC CCT ACA GAG TGG TCC ATT TAT TAC AGC TGC TGA ACC CAC
       1720         1730         1740         1750
        *            *            *            *
ACT GAC ACG CTG TTA TCA CTC AGA GCC TGG CAG TTT ACA GAG GCT
    1760         1770         1780         1790         1800
     *            *            *            *            *
CAC TCT CCG NTA TGT GTC CTG TGN TTT GAA CAA ATG TAT AAT GAC
       1810         1820         1830         1840
        *            *            *            *
TTT ATT CAT TGT TTT TTA ATG AAG CTG ATC TTT TCC CTC TGA AAC
    1850         1860         1870         1880         1890
     *            *            *            *            *
TAC AAA ATG AAT TTC TAG CAT AGC CAT AGC AGG TGT CAA GCT ATA
       1900         1910         1920         1930
        *            *            *            *
CTA CTA GGT AAA TTT TAA GAA ATG CCC AAC TTT ATC ATA TTT GCA
    1940         1950         1960         1970         1980
     *            *            *            *            *
TTT CAA AAT ATG ATT AAT CAC ACA TAG GAT TTT GTT TCT TCA TGC
       1990         2000         2010         2020
        *            *            *            *
CTA CAG CAA ATA GAA ATA AAG TGC AAG AAA CTT TTC TGA GGC AAA
```

FIG.8b-3

```
      2030         2040          2050          2060          2070
       *            *             *             *             *
GCT TTC ACT TTG TGA ACG TAA AAT GTT GAC TCT AAT ATT TTC CAT
             2080          2090          2100          2110
              *             *             *             *
ACT GTA GTA TAT GTG TGT GTA TTA TGT GAG GAT TCA TAG TCT GCT
      2120         2130          2140          2150          2160
       *            *             *             *             *
CTT ACT TTT TTA TAG TAG CTA AGA ATT ATT ATA ATC GCT ATA AGC
             2170          2180          2190          2200
              *             *             *             *
AGA AAC AAT TAT TCT TAA CAA AAT GAA TAC ACA CAA GAA AAG CTT
      2210         2220          2230          2240          2250
       *            *             *             *             *
TAG TTT AGC TAT TAG AAC TAA CTC TAT AAT TAT GAT AAC CAT GAG
             2260          2270          2280          2290
              *             *             *             *
ATG CTG GAA CAG GAG CCA GCA GAA GCC ACA GCC CTC TGA TAT TAA
      2300         2310          2320          2330          2340
       *            *             *             *             *
TAT ATA AAG AAA CCA AAA TCT GCT TGT TAA ACT GAG GCA GTT GTA
             2350          2360          2370          2380
              *             *             *             *
TGG ATA CTT CAA CCT GAA AAT GCC CCC TTC TTC CTG AAA CAG AAC
      2390         2400          2410          2420          2430
       *            *             *             *             *
ATT TAA TAA AAA TGG CAT GCT TGG ACA GGA ATT TCT TTT TTA AAA
             2440
              *
AAT GCT TAG TTT TTA TG
```

FIG.8b-4

```
         10              20              30              40
          *               *               *               *
TTC CTT TAT CTC CTA GAT ACA CCA AGA TGA AGA CTG CCA CCA ACA
     50              60              70              80              90
      *               *               *               *               *
TCT ACA TTT TCA ACC TTG CTC TGC AGA TGC CTT AGC CAC CAG TAC
            100             110             120             130
             *               *               *               *
CCT GCC CTT CCA GAG TGT GAA TTA CCT AAT GGG AAC ATG GCC ATT
    140             150             160             170             180
     *               *               *               *               *
TGG AAC CAT CCT TTG CAA GAT AGT GAT CTC CAT AGA TTA CTA TAA
        190             200             210             220
         *               *               *               *
CAT GTT CAC CAG CAT ATT CAC CCT CTG CAC CAT GAG TGT TGA TCG
    230             240             250             260             270
     *               *               *               *               *
ATA CAT TGC AGT CTG CCA CCC TGT CAA GGC CTT AGA TTT CCG TAC
            280             290             300             310
             *               *               *               *
TCC CNN NNN NNN NNN NNN NNN NNN NNN NNN NNN NNN NNN NNN NNN
    320             330             340             350             360
     *               *               *               *               *
NNN NNN NNN NNN NNN NNN NNN NNN NNN NNN NNN NNN NNN NNN NNN
            370             380             390             400
             *               *               *               *
NNN NNN NNG TTC CAT AGA TTG TAC ACT AAC ATT CTC TCA TCC AAC
    410             420             430             440             450
     *               *               *               *               *
CTG GTA CTG GGA AAA CCT GCT GAA GAT CTG TGT TTT CAT CTT CGC
```

FIG.8c-1

```
            460         470         480         490
             *           *           *           *
CTT CAT TAT GCC AGT GCT CAT CAT TAC CGT GTG CTA TGG ACT GAT
      500         510         520         530         540
       *           *           *           *           *
GAT CTT GCG CCT CAA GAG TGT CCG CAT GCT CTC TGG CTC CAA AGA
            550         560         570         580
             *           *           *           *
AAA GGA CAG GAA TCT TCG AAG GAT CAC CAG GAT GGT GCT GGT GGT
      590         600         610         620         630
       *           *           *           *           *
GGT GGC TGT GTT CAT CGT CTG CTG GAC TCC CAT TCA CAT TTA CGT
            640         650         660         670
             *           *           *           *
CAT CAT TAA AGC CTT GGT TAC AAT CCC AGA AAC TAC GTT CCA GAC
      680         690         700         710         720
       *           *           *           *           *
TGT TTC TTG GCA CTT CTG CAT TGC TCT AGG TTA CAC AAA CAG CTG
            730         740         750         760
             *           *           *           *
CCT CAA CCC AGT CCT TTA TGC ATT TCT GGA TGA AAA CTT CCA CGA
      770         780         790         800         810
       *           *           *           *           *
TGC TTC AGA GAG TTC TGT ATC CCA ACC TCT TCC AAC ATT GAG CAA
            820         830
             *           *
CAA AAC TCC ACT CGA ATT CC
```

FIG.8c-2

```
           10          20          30          40
            *           *           *           *
GGG TAC CGG GCC CCC CCT CGA GGT CGA CGG TAT CGA TAA GCT TGA
       50          60          70          80          90
        *           *           *           *           *
TAT CGA ATT CTT ACT GAA TTA GGT ATC TTT CTT CAC ACT ACT TGG
          100         110         120         130
            *           *           *           *
TAA AAA AAA TGA AAA GGC AGA AAA ATT AGC CCC AAA AGA GAT GAA
      140         150         160         170         180
        *           *           *           *           *
ACT CTT CCG TCC ATC ACC ATT GAC TCT ATT GTG AAC TTA TGA AAA
          190         200         210         220
            *           *           *           *
AGG TAG TTG AGC AAT ATG AAG GCC ATG ATG TGG AAT TAA ACA CAC
      230         240         250         260         270
        *           *           *           *           *
ACA CAC ACA CAC ACA CAC ACA CAC ACA CAT GCT GGA TTC TAA ATG
          280         290         300         310
            *           *           *           *
TGT CCT TCC TCC TCT CAC TCT CTT GAT TCA AGT TTA TTT CTG AAC
      320         330
        *           *
TGA GAC ACG ATC ACC AC
```

FIG.8d

```
         10          20          30          40
CGG ATC CTT AGC ATC CCC AAA GCG CCT CCG TGT ACT TCT AAG GTG
     50          60          70          80          90
GGA GGG GGA TAC AAG CAG AGG AGA ATA TCG GAC GCT CAG ACG TTC
         100         110         120         130
CAT TCT GCC TGC CGC TCT TCT CTG GTT CCA CTA GGG CTT GTC CTT
     140         150         160         170         180
GTA AGA AAC TGA CGG AGC CTA GGG CAG CTG TGA GAG GAA GAG GCT
         190         200         210         220
GGG GCG CCT GGA ACC CGA ACA CTC TTG AGT GCT CTC AGT TAC AGN
     230         240         250         260         270
CTA CCG AGT CCG CAG GAA GCA TTC AGA ACC ATG GAC AGC AGC GCC
         280         290         300         310
GGC CCA GGG AAC ATC AGC GAC TGC TCT GAC CCC TTA GCT CCT GCA
     320         330         340         350         360
AGT TGC TCC CCA GCA CCT GGC TCC TGG CTC AAC TTG TCC CAC GTT
         370         380         390         400
GAT GGA AAC CAG TCC GAC CCA TGC GGT CCT AAC CCG ACG GGC CTT
     410         420         430         440         450
GGC GGG AAC GAC AGC CTG TGC CCT CAG ACC GGC AGC CCT TCC ATG
         460         470         480         490
GTC ACA GCC ATC ACC ATC ATG GCC CTC TAT TCT ATC GTG TGT GTA
     500         510         520         530         540
GTG GGC CTC TTT GGA AAC TTC CTG GTC ATG TAT GTG ATT GTA AGA
         550         560         570         580
TAT ACC AAA ATG AAG ACT GCC ACC AAC ATC TAC ATT TTC AAC CTT
     590         600         610         620         630
GCT CTG GCA GAT GCC TTA GCC ACT AGC ACG CTG CCC TTT CAG AGT
         640         650         660         670
GTT AAC TAC CTG ATG GGA ACG TGG CCC TTT GGA AAC ATC CTC TGC
```

FIG.9a

```
       680           690           700           710           720
AAG ATC GTG ATC TCA ATA GAC TAC TAC AAC ATG TTC ACC AGT ATC
             730           740           750           760
TTC ACC CTC TGC ACC ATG AGT GTA GAC CGC TAC ATT GCC GTC TGC
       770           780           790           800           810
CAC CCG GTC AAG GCC CTG GAT TTC CGT ACC CCC CGA AAT GCC AAA
             820           830           840           850
ATT GTC AAT GTC TGC AAC TGG ATC CTC TCT TCT GCC ATT GGT CTG
       860           870           880           890           900
CCC GTA ATG TTC ATG GCA ACC ACA AAA TAC AGG CAG GGG TCC ATA
             910           920           930           940
GAT TGC ACC CTC ACG TTC TCT CAT CCC ACA TGG TAC TGG GAG AAC
       950           960           970           980           990
CTG CTC AAA ATC TGT GTC TTC ATC TTC GCC TTC ATC ATG CCG GGC
             1000          1010          1020          1030
CTC ATC ATC ACT GTG TGT TAT GGA CTG ATG ATC TTA CAG CTC AAG
       1040          1050          1060          1070          1080
AGT GTC CGC ATG CTG TCG GGC TCC AAA GAA AAG GAC AGG AAC CTG
             1090          1100          1110          1120
CGC AGG ATC ACC CGG ATG GTG CTG GTG GTC GTG GCT GTA TTT ATT
       1130          1140          1150          1160          1170
GTC TGC TGG ACC CCC ATC CAC ATC TAT GTC ATC ATC AAA GCA CTG
             1180          1190          1200          1210
ATC ACG ATT CCA GAA ACC ACT TTC CAG ACT GTT TCC TGG CAC TTC
       1220          1230          1240          1250          1260
TGC ATT GCC TTG GGT TAC ACA AAC AGC TGC CTG AAC CCA GTT CTT
             1270          1280          1290          1300
TAT GCG TTC CTG GAT GAA AAC TTC AAA CGA TGT TTT AGA GAG TTC
       1310          1320          1330          1340          1350
TGC ATC CCA ACT TCC TCC ACA ATC GAA CAG CAA AAC TCT GCT CGA
```

FIG.9b

```
            1360          1370          1380          1390
ATC CGT CAA AAC ACT AGG GAA CAC CCC TCC ACG GCT AAT ACA GTG
     1400          1410          1420          1430          1440
GAT CGA ACT AAC CAC CAG CTA GAA AAT CTG GAA GCA GAA ACT GCT
          1450          1460          1470          1480
CCA TTG CCC TAA CTG GGT CCC ACG CCA TCC AGA CCC TCG CTA AAC
     1490          1500          1510          1520          1530
TTA GAG GCT GCC ATC TAC TTG GAA TCA GGT TGC TGT CAG GGT TTG
          1540          1550          1560          1570
TGG GAG GCT CTG GTT TCC TGG AAA AGC ATC TGA TCC TGC ATC ATT
     1580          1590          1600          1610          1620
CAA AGT CAT TCC TCT CTG GCT ATT CAC GCT ACA CGT CAG AGA CAC
          1630          1640          1650          1660
TCA GAC TGT GTC AAG CAC TCA GAA GGA AGA GAC TGC AGG CCA CTA
     1670          1680          1690          1700          1710
CTG AAT CCA GCT CAT GTA CAG AAA CAT CCA ATG GAC CAC AAT ACT
          1720          1730          1740          1750
CTG TGG TAT GTG ATT TGT GAT CAA CAT AGA AGG TGA CCC TTC CCT
     1760          1770          1780          1790          1800
ATG TGG AAT TTT TAA TTT CAA GGA AAT ACT TAT GAT CTC ATC AAG
          1810          1820          1830          1840
GGA AAA ATA GAT GTC ACT TGT TAA ATT CAC TGT AGT GAT GCA TAA
     1850          1860          1870          1880          1890
AGG AAA AGC TAC CTC TGA CCT CTA GCC CAG TCA CCC TCT ATG GAA
          1900          1910          1920          1930
AGT TCC ATA GGG AAT ATG TGA GGG AAA ATG TTG CTT CCA AAT TAA
     1940          1950          1960          1970          1980
ATT TTC ACC TTT ATG TTA TAG TCT AGT TAA GAC ATC AGG GGC ATC
T
```

FIG.9c

HIGH HOMOLOGY BETWEEN DELTA, MU AND KAPPA OPIOD RECEPTORS

```
                         10          20          30          40          50
                          *           *           *           *           *
DOR-1                                MELVPSARAELQSSPLVNLSDAFPSAFPSAGANASGSPGARSASSLALAI
rMORa     mdsstgpgntsdcsdplaqasccspapgswlnlShvdgNqSDpcglnrtglGgNdSlcPqt-gspSmvtAI>
                10          20          30          40          50          60
rKORa                     mespiqifrgdgptcspsacllpnssswfpnwaesdsngsvgsedqqlesahiSpAipv>
                                      10          20          30          40          50          60
                          *           *           *           *           *           *
                         60          70          80          90         100         110         120
                          *           *           *           *           *           *           *
DOR-1     AITALYSAVCAVGLLGNVLVMFGIVRYTKLKTATNIYIFNLALADALATSTLPFQSAKYLMETWPFGELL
rMORa     tImALYSiVCvVGLfGNfLVMvvIVRYTKmKTATNIYIFNLALADALATSTLPFQSvnYLMgTWPFGtiL>
                70          80          90         100         110         120         130
rKORa     iITAvYSvVFvVGLVGNSLVMFvIiRYTKmKTATNIYIFNLALADALVTtTmPFQSAvYYLMnsWPFGdvL>
                70          80          90         100         110         120         130
                          *           *           *           *           *           *
                        130         140         150         160         170         180         190
                          *           *           *           *           *           *           *
DOR-1     CKAVLSIDYYNMFTSIFTLTMMSVDRYIAVCHPVKALDFRTPAKAKLINICIWVLASGVGVPIMVMAVTQ
rMORa     CKiViSIDYYNMFTSIFTLCtMSVDRYIAVCHPVKALDFRTPrnAKivNvCnWiLsSaiGIPvMfMAtTk>
                140         150         160         170         180         190         200
rKORa     CKiViSIDYYNMFTSIFTLTMMSVDRYIAVCHPVKALDFRTPlKAKiINICIWlLASSVGisaiVlggTk>
                140         150         160         170         180         190         200
                          *           *           *           *           *           *
```

FIG. 10a

```
DOR-1    PRDGAVVCMLQFPSPSWYWDTVTKICVFLFAFVVPILIITVCYGLMLLRLRSVRLLSGSKEKDRSLRRIT
           200       210       220       230       240       250       260
            *         *         *         *         *         *         *
rMORa    yRqGsidCtLtFshPtWYwenllKICVFiFAFimPILIITVCYGLMiLRLkSVRmLSGSKEKDRnLRRIT>
         vd                              ys
           210       220       230       240       250       260       270
            *         *         *         *         *         *         *
rKORa    vRedvieCsLQFPddeW-WDIfmKICVFvFAFViPvLIIiVCYtLMiLRLkSVRLLSGSrEKDRnLRRIT>
                |210

270       280       290       300       310       320       330
            *         *         *         *         *         *         *
DOR-1    RMVLVVVGAFVVCWAPIHIFVIWTLVDINRRDPLVVAALHLCIALGYANSSLNPVLYAFLDENFKRCFR
           280       290       300       310       320       330       340
            *         *         *         *         *         *         *
rMORa    RMVLVVVavFiVCWtPIHIyVIikaLiTi-pettfgtvsWHfCIALGYtNSclNPVLYAFLDENFKRCFR>
           280       290       300       310       320       330       340
            *         *         *         *         *         *         *
rKORa    klVLVVVavFiiCWtPIHIFIilVeaLgstshsta-alssyyfCIALGYtNSSLNPVLYAFLDENFKRCFR>

340       350       360       370
            *         *         *         *
DOR-1    QLCRTPCGRQEPGSLRRPRQATTRERVTACTPSDGPGGGAAA
           350       360       370       380
            *         *         *         *
rMORa    efCiptsstiEqqnstRvRQ-nTREhpstantvDrtnhqlenleaetaplp
           350       360
            *         *
rKORa    dfCfpikmRmErqStnRvRn-TvqdpasmrdvggmnkpV>

Identical amino acids between DOR-1 and mu and kappa receptors in upper
case Predicted transmembrane domains are underlined
```

FIG. 10b

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: single
      (D) TOPOLOGY: linear (xi) SEQUENCE DESCRIPTION: SEQ ID NO:1:

Tyr Gly Gly Phe Met
1          5

(2) INFORMATION FOR SEQ ID NO:2:

(i) SEQUENCE CHARACTERISTICS:
      (A) LENGTH: 5 amino acids
      (B) TYPE: amino acid
      (C) STRANDEDNESS: single
      (D) TOPOLOGY: linear (xi) SEQUENCE DESCRIPTION: SEQ ID NO:2:

Tyr Gly Gly Phe Leu
1          5

(2) INFORMATION FOR SEQ ID NO:3:

(i) SEQUENCE CHARACTERISTICS:
      (A) LENGTH: 6 amino acids
      (B) TYPE: amino acid
      (C) STRANDEDNESS: single
      (D) TOPOLOGY: linear (ix) FEATURE:
      (A) NAME/KEY: Modified-site
      (B) LOCATION: 2
      (D) OTHER INFORMATION: /note= "D form of amino acid"

(xi) SEQUENCE DESCRIPTION: SEQ ID NO:3:

Tyr Ser Gly Phe Leu Thr
1          5

(2) INFORMATION FOR SEQ ID NO:4:

(i) SEQUENCE CHARACTERISTICS:
      (A) LENGTH: 5 amino acids
      (B) TYPE: amino acid
      (C) STRANDEDNESS: single
      (D) TOPOLOGY: linear (ix) FEATURE:
      (A) NAME/KEY: Modified-site
      (B) LOCATION: group(2, 5)
      (D) OTHER INFORMATION: /product= "OTHER"
          /note= "D-penicillamine"

(xi) SEQUENCE DESCRIPTION: SEQ ID NO:4:

Tyr Xaa Gly Phe Xaa
1          5

(2) INFORMATION FOR SEQ ID NO:5:

(i) SEQUENCE CHARACTERISTICS:
      (A) LENGTH: 5 amino acids (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /note= "D form of amino acid"

(ix) FEATURE:
        (A) NAME/KEY: Modified-site
        (B) LOCATION: 5
        (D) OTHER INFORMATION: /note= "D form of amino acid"

(xi) SEQUENCE DESCRIPTION: SEQ ID NO:5:

Tyr Ala Gly Phe Leu
1               5

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 2
        (D) OTHER INFORMATION: /note= "D form of amino acid"

(ix) FEATURE:
        (A) NAME/KEY: Modified-site
        (B) LOCATION: 4
        (D) OTHER INFORMATION: /product= "MePhe"
            /note= "N-Methylphenylalanine"

(ix) FEATURE:
        (A) NAME/KEY: Modified-site
        (B) LOCATION: 5
        (D) OTHER INFORMATION: /product= "Gly-ol"
            /note= "Carboxy end of glycine has been replaced with
            an alcohol substituent"

(xi) SEQUENCE DESCRIPTION: SEQ ID NO:6:

Tyr Ala Gly Xaa Xaa
1               5

(2) INFORMATION FOR SEQ ID NO:7:

(i) SEQUENCE CHARACTERISTICS:
        (A) LENGTH: 1829 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 29..1144

(xi) SEQUENCE DESCRIPTION: SEQ ID NO:7:

```
GCACGGTGGA GACGGACACG GCGGCGCC ATG GAG CTG GTG CCC TCT GCC CGT        52
                               Met Glu Leu Val Pro Ser Ala Arg
                                1               5

GCG GAG CTG CAG TCC TCG CCC CTC GTC AAC CTC TCG GAC GCC TTT CCC      100
Ala Glu Leu Gln Ser Ser Pro Leu Val Asn Leu Ser Asp Ala Phe Pro
     10              15                  20

AGC GCC TTC CCC AGC GCG GGC GCC AAT GCG TCG GGG TCG CCG GGA GCC      148
Ser Ala Phe Pro Ser Ala Gly Ala Asn Ala Ser Gly Ser Pro Gly Ala
 25              30                  35                  40

CGT AGT GCC TCG TCC CTC GCC CTA GCC ATC GCC ATC ACC GCG CTC TAC      196
```

-continued

```
                Arg Ser Ala Ser Ser Leu Ala Leu Ala Ile Ala Ile Thr Ala Leu Tyr
                                45                  50                  55

TCG GCT GTG TGC GCA GTG GGG CTT CTG GGC AAC TGT CTC GTC ATG TTT              244
Ser Ala Val Cys Ala Val Gly Leu Leu Gly Asn Cys Leu Val Met Phe
            60                  65                  70

GGC ATC GTC CGG TAC ACC AAA TTG AAG ACC GCC ACC AAC ATC TAC ATC              292
Gly Ile Val Arg Tyr Thr Lys Leu Lys Thr Ala Thr Asn Ile Tyr Ile
            75                  80                  85

TTC AAT CTG GCT TTG GCT GAT GCG CTG GCC ACC AGC ACG CTG CCC TTC              340
Phe Asn Leu Ala Leu Ala Asp Ala Leu Ala Thr Ser Thr Leu Pro Phe
            90                  95                 100

CAG AGC GCC AAG TAC TTG ATG GAA ACG TGG CCG TTT GGC GAG CTG CTG              388
Gln Ser Ala Lys Tyr Leu Met Glu Thr Trp Pro Phe Gly Glu Leu Leu
105                 110                 115                 120

TGC AAG GCT GTG CTC TCC ATT GAC TAC TAC AAC ATG TTC ACT AGC ATC              436
Cys Lys Ala Val Leu Ser Ile Asp Tyr Tyr Asn Met Phe Thr Ser Ile
                125                 130                 135

TTC ACC CTC ACC ATG ATG AGC GTG GAC CGC TAC ATT GCT GTC TGC CAT              484
Phe Thr Leu Thr Met Met Ser Val Asp Arg Tyr Ile Ala Val Cys His
                140                 145                 150

CCT GTC AAA GCC CTG GAC TTC CGG ACA CCA GCC AAG GCC AAG CTG ATC              532
Pro Val Lys Ala Leu Asp Phe Arg Thr Pro Ala Lys Ala Lys Leu Ile
                155                 160                 165

AAT ATA TGC ATC TGG GTC TTG GCT TCA GGT GTC GGG GTC CCC ATC ATG              580
Asn Ile Cys Ile Trp Val Leu Ala Ser Gly Val Gly Val Pro Ile Met
170                 175                 180

GTC ATG GCA GTG ACC CAA CCC CGG GAT GGT GCA GTG GTA TGC ATG CTC              628
Val Met Ala Val Thr Gln Pro Arg Asp Gly Ala Val Val Cys Met Leu
185                 190                 195                 200

CAG TTC CCC AGT CCC AGC TGG TAC TGG GAC ACT GTG ACC AAG ATC TGC              676
Gln Phe Pro Ser Pro Ser Trp Tyr Trp Asp Thr Val Thr Lys Ile Cys
                205                 210                 215

GTG TTC CTC TTT GCC TTC GTG GTG CCG ATC CTC ATC ATC ACG GTG TGC              724
Val Phe Leu Phe Ala Phe Val Val Pro Ile Leu Ile Ile Thr Val Cys
                220                 225                 230

TAT GGC CTC ATG CTA CTG CGC CTG CGC AGC GTG CGT CTG CTG TCC GGT              772
Tyr Gly Leu Met Leu Leu Arg Leu Arg Ser Val Arg Leu Leu Ser Gly
                235                 240                 245

TCC AAG GAG AAG GAC CGC AGC CTG CGG CGC ATC ACG CGC ATG GTG CTG              820
Ser Lys Glu Lys Asp Arg Ser Leu Arg Arg Ile Thr Arg Met Val Leu
250                 255                 260

GTG GTG GTG GGC GCC TTC GTG GTG TGC TGG GCG CCC ATC CAC ATC TTC              868
Val Val Val Gly Ala Phe Val Val Cys Trp Ala Pro Ile His Ile Phe
265                 270                 275                 280

GTC ATC GTC TGG ACG CTG GTG GAC ATC AAT CGG CGC GAC CCA CTT GTG              916
Val Ile Val Trp Thr Leu Val Asp Ile Asn Arg Arg Asp Pro Leu Val
                285                 290                 295

GTG GCC GCA CTG CAC CTG TGC ATT GCG CTG GGC TAC GCC AAC AGC AGC              964
Val Ala Ala Leu His Leu Cys Ile Ala Leu Gly Tyr Ala Asn Ser Ser
                300                 305                 310

CTC AAC CCG GTT CTC TAC GCC TTC CTG GAC GAG AAC TTC AAG CGC TGC             1012
Leu Asn Pro Val Leu Tyr Ala Phe Leu Asp Glu Asn Phe Lys Arg Cys
                315                 320                 325

TTC CGC CAG CTC TGT CGC ACG CCC TGC GGC CGC CAA GAA CCC GGC AGT             1060
Phe Arg Gln Leu Cys Arg Thr Pro Cys Gly Arg Gln Glu Pro Gly Ser
                330                 335                 340

CTC CGT CGT CCC CGC CAG GCC ACC ACG CGT GAG CGT GTC ACT GCC TGC             1108
Leu Arg Arg Pro Arg Gln Ala Thr Thr Arg Glu Arg Val Thr Ala Cys
345                 350                 355                 360
```

```
ACC CCC TCC GAC GGC CCG GGC GGT GGC GCT GCC GCC TGACCTACCC         1154
Thr Pro Ser Asp Gly Pro Gly Gly Gly Ala Ala Ala
            365                     370

GACCTTCCCC TTAAACGCCC CTCCCAAGTG AAGTGATCAG AGGCCACACC GAGCTCCCTG  1214

GGAGGCTGTG GCCACCACCA GGACAGCTAG AATTGGGCCT GCACAGAGGG GAGGCCTCCT  1274

GTGGGGACGG GCCTGAGGGA TCAAAGGCTC CAGGTTGGAA CGGTGGGGGT GAGGAAGCAG  1334

AGCTGGTGAT TCCTAAACTG TATCCATTAG TAAGGCCTCT CAATGGGACA GAGCCTCCGC  1394

CTTGAGATAA CATCGGGTTC TGGCCTTTTT GAACACCCAG CTCCAGTCCA AGACCCAAGG  1454

ATTCCAGCTC CAGAACCAGG AGGGGCAGTG ATGGGTCGA TGATTTGGTT TGGCTGAGAG   1514

TCCCAGCATT TGTGTTATGG GGAGGATCTC TCATCTTAGA GAAGAAAGGG GACAGGGCAT  1574

TCAGGCAAGG CAGCTTGGGG TTTGGTCAGG AGATAAGCGC CCCCCTTCCC TTGGGGGGAG  1634

GATAAGTGGG GGATGGTCAC GTTGGAGAAG AGTCAAAGTT CTCACCACCT TTCTAACTAC  1694

TCAGCTAAAC TCGTTGAGGC TAGGGCCAAC GTGACTTCTC TGTAGAGAGG TACAAGCCGG  1754

GCCTGATGGG GCAGGCCTGT GTAATCCCAG TCATAGTGGA GGCTGAGGCT GGAAAATTAA  1814

GGACCAACAG CCCGG                                                   1829

(2) INFORMATION FOR SEQ ID NO:8:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:8:

Met Glu Leu Val Pro Ser Ala Arg Ala Glu Leu Gln Ser Ser Pro Leu
 1               5                  10                  15

Val Asn Leu Ser Asp Ala Phe Pro Ser Ala Phe Pro Ser Ala Gly Ala
            20                  25                  30

Asn Ala Ser Gly Ser Pro Gly Ala Arg Ser Ala Ser Ser Leu Ala Leu
        35                  40                  45

Ala Ile Ala Ile Thr Ala Leu Tyr Ser Ala Val Cys Ala Val Gly Leu
    50                  55                  60

Leu Gly Asn Cys Leu Val Met Phe Gly Ile Val Arg Tyr Thr Lys Leu
65                  70                  75                  80

Lys Thr Ala Thr Asn Ile Tyr Ile Phe Asn Leu Ala Leu Ala Asp Ala
                85                  90                  95

Leu Ala Thr Ser Thr Leu Pro Phe Gln Ser Ala Lys Tyr Leu Met Glu
            100                 105                 110

Thr Trp Pro Phe Gly Glu Leu Leu Cys Lys Ala Val Leu Ser Ile Asp
        115                 120                 125

Tyr Tyr Asn Met Phe Thr Ser Ile Phe Thr Leu Thr Met Met Ser Val
    130                 135                 140

Asp Arg Tyr Ile Ala Val Cys His Pro Val Lys Ala Leu Asp Phe Arg
145                 150                 155                 160

Thr Pro Ala Lys Ala Lys Leu Ile Asn Ile Cys Ile Trp Val Leu Ala
                165                 170                 175

Ser Gly Val Gly Val Pro Ile Met Val Met Ala Val Thr Gln Pro Arg
            180                 185                 190

Asp Gly Ala Val Val Cys Met Leu Gln Phe Pro Ser Pro Ser Trp Tyr
        195                 200                 205
```

-continued

```
Trp Asp Thr Val Thr Lys Ile Cys Val Phe Leu Phe Ala Phe Val Val
    210                 215                 220

Pro Ile Leu Ile Ile Thr Val Cys Tyr Gly Leu Met Leu Leu Arg Leu
225                 230                 235                 240

Arg Ser Val Arg Leu Leu Ser Gly Ser Lys Glu Lys Asp Arg Ser Leu
                245                 250                 255

Arg Arg Ile Thr Arg Met Val Leu Val Val Gly Ala Phe Val Val
                260                 265                 270

Cys Trp Ala Pro Ile His Ile Phe Val Ile Val Trp Thr Leu Val Asp
            275                 280                 285

Ile Asn Arg Arg Asp Pro Leu Val Val Ala Ala Leu His Leu Cys Ile
    290                 295                 300

Ala Leu Gly Tyr Ala Asn Ser Ser Leu Asn Pro Val Leu Tyr Ala Phe
305                 310                 315                 320

Leu Asp Glu Asn Phe Lys Arg Cys Phe Arg Gln Leu Cys Arg Thr Pro
                325                 330                 335

Cys Gly Arg Gln Glu Pro Gly Ser Leu Arg Arg Pro Arg Gln Ala Thr
            340                 345                 350

Thr Arg Glu Arg Val Thr Ala Cys Thr Pro Ser Asp Gly Pro Gly Gly
    355                 360                 365

Gly Ala Ala Ala
    370
```

(2) INFORMATION FOR SEQ ID NO:9:

(i) SEQUENCE CHARACTERISTICS:
        (A) LENGTH: 369 amino acids
        (B) TYPE: amino acid
        (C) STRANDEDNESS: single
        (D) TOPOLOGY: linear (xi) SEQUENCE DESCRIPTION: SEQ ID NO:9:

```
Met Glu Leu Thr Ser Glu Gln Phe Asn Gly Ser Gln Val Trp Ile Pro
1               5                   10                  15

Ser Pro Phe Asp Leu Asn Gly Ser Leu Gly Pro Ser Asn Gly Ser Asn
                20                  25                  30

Gln Thr Glu Pro Tyr Tyr Asp Met Thr Ser Asn Ala Val Leu Thr Phe
            35                  40                  45

Ile Tyr Phe Val Val Cys Val Val Gly Leu Cys Gly Asn Thr Leu Val
    50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
                100                 105                 110

Ala Ile Cys Arg Val Val Met Thr Val Asp Gly Ile Asn Gln Phe Thr
            115                 120                 125

Ser Ile Phe Cys Leu Thr Val Met Ser Ile Asp Arg Tyr Leu Ala Val
    130                 135                 140

Val His Pro Ile Lys Ser Ala Lys Trp Arg Arg Pro Arg Thr Ala Lys
145                 150                 155                 160

Met Ile Asn Val Ala Val Trp Gly Val Ser Leu Leu Val Ile Leu Pro
                165                 170                 175

Ile Met Ile Tyr Ala Gly Leu Arg Ser Asn Gln Trp Gly Arg Ser Ser
                180                 185                 190
```

```
Cys Thr Ile Asn Trp Pro Gly Glu Ser Gly Ala Trp Tyr Thr Gly Phe
            195                 200                 205

Ile Ile Tyr Ala Phe Ile Leu Gly Phe Leu Val Pro Leu Thr Ile Ile
            210                 215                 220

Cys Leu Cys Tyr Leu Phe Ile Ile Lys Val Lys Ser Ser Gly Ile
225                 230                 235                 240

Arg Val Gly Ser Ser Lys Arg Lys Ser Glu Lys Lys Val Thr Arg
                245                 250                 255

Met Val Ser Ile Val Val Ala Val Phe Ile Phe Cys Trp Leu Pro Phe
                260                 265                 270

Tyr Ile Phe Asn Val Ser Ser Val Ser Val Ala Ile Ser Pro Thr Pro
            275                 280                 285

Ala Leu Lys Gly Met Phe Asp Phe Val Val Ile Leu Thr Tyr Ala Asn
            290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Ala Glu
                325                 330                 335

Asp Gly Glu Arg Ser Asp Ser Lys Gln Asp Lys Ser Arg Leu Asn Glu
                340                 345                 350

Thr Thr Glu Thr Gln Arg Thr Leu Leu Asn Gly Asp Leu Gln Thr Ser
            355                 360                 365

Ile
```

(2) INFORMATION FOR SEQ ID NO:10:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (xi) SEQUENCE DESCRIPTION: SEQ ID NO:10:

```
GGGCAGTGGT GTGCATGCTC CAGTTCCCCA GCCCCAGCTG GTACTGGGAC ACGGTGACCA      60

AGATCTGCGT GTTCCTCTTC GCCTTCGTGG TGCCCATCCT CATCATCACC GTGTGCTATG     120

GCCTCATGCT                                                            130
```

(2) INFORMATION FOR SEQ ID NO:11:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (xi) SEQUENCE DESCRIPTION: SEQ ID NO:11:

```
GGTGCAGTGG TATGCATGCT CCAGTTCCCC AGTCCCAGCT GGTACTGGGA CACTGTGACC      60

AAGATCTGCG TGTTCCTCTT TGCCTTCGTG GTGCCGATCC TCATCATCAC GGTGTGCTAT     120

GGCCTCATGC                                                            130
```

(2) INFORMATION FOR SEQ ID NO:12:

(i) SEQUENCE CHARACTERISTICS:
        (A) LENGTH: 2447 base pairs
        (B) TYPE: nucleic acid
        (C) STRANDEDNESS: single
        (D) TOPOLOGY: linear -continued (xi) SEQUENCE DESCRIPTION: SEQ ID NO:12:

```
CCTGGCCTTT TGGGGATGTG CTGTGCAAGA TAGTAATTTC CATTGATTAC TACAACATGT      60
TCACCAGCAT CTTCACCTTG ACCATGATGA GCGTGGACCG CTACATTGCC GTGTGCCACC     120
CCGTGAAGGC TTTGGACTTC CGCACACCCT TGAAGGCAAA GATCATCAAT ATCTGCATCT     180
GGCTGCTGTC GTCATCTGTT GGCATCTCTG CAATAGTCCT TGGAGGCACC AAAGTCAGGG     240
AAGGTAAGAG CAGTCATTTC ATTCTGTTCA TAAAAATGTA GCTTCAAATT ACATAGACTT     300
TTAATTTGAG CGTGAGTAGG CCACATATTT GTGGAAATCG ATGCCAAAAG ACGACGGAAA     360
TGTAGTGCCT AAATCCATGG AAGATGAGAA GTAGAACAAT TTTTTGTCCC TTTCCACCTC     420
TAAACACAGA ATGCAATAAT GACATTGCCA AGAGAGAGAT GCCCGACCTG TCTCCCATTC     480
TGGCAATGTT TAGTAGAAAG TGGAGGGGTG AGGATGAGGT AAGAACCACA GGCATGTAGA     540
TTTTAAAGTA CAACCTGGCA AGTCCAGACA CACCTTCTCA CTCCTTTTTT TCTCTTTAAC     600
AAGGGATATA AATTATTGGT GACATATGCT GGTTGTTTCC TCTTTTATTC CTAAAGGATA     660
ACCTCCAAAT CACTATTTTA ACAGCTTTGG CGTAGGATCT CAAAATCAAG TTAACGGATG     720
GTAGTTACAG ATGAGTCAGA ACCACTTGAT TTGGACATAT CAGGTTTTCC CTTGCAAACC     780
AGCCAACTGA TTTTTTTTTT TTTTTTTTTT GAGAGAGAGT CTTGCTCTGT TGCCAGGCTA     840
GAGTGCAGTG GCGCGATATC GGCTCACTGC AACCTCTGCC TCCCGGGTTC AACCTCAGCC     900
TCTCGAGTAG CTGGGACTAC TGGCACACAC CACCATGCCC AGCTAATTTT TGTATTTTTA     960
GTAGAGACAG GGTTTCACCG TGTTGGCCAG GGTGGTCTCA ATCTCTTGAC CTCGTGATCT    1020
GCCCGCCTCG NCTCCCCAAA GTGCTGGGAT TACAGGCGTG CNCTGCNCCC GNCCCTGTT     1080
GATGTTTTTC CTGTATTTCT AGGACAGTAG TTCTCACTCT GGGCTGCACA TTGGAATCAC    1140
CTGGGTACTT TAGAAAACAC TGCTGCCTGC ATCCCACCCC TTAAGGGTCT GGTGTAATTG    1200
ACCTGGGGTA CAGCCTGGGT GTCAAGATTT TTGAGCTCTC TCCAGGTGAC TCTGACCTGC    1260
AGCCAAGGTG AGAGGTACTG TTCTAGGAGT TTTGCTTTAC TAGCAAAATA TAAAGCTATA    1320
GAAAGCATCT TTTGTTCCTC ATAGAAATTA ATGATGGGA GGTGAGCAGA ATAGTCACTC     1380
TGGGCCTACT CATGCTGTTT AATGCTCCAG CAGGTATATA GGTTCTCCAG TTACTAGGGG    1440
GTTCATAATA CCTGTGAGAG CAGATAACTG AGTGTATATA GTGAGGATTT CCAGGTCATA    1500
GTGAAAGGGC AAGGCACTAA AATCATAGCT TGTCTTGCAT ATACTGTTTG TTTGTTTTTA    1560
GACTTACATG TTAGGTTTCA GTTTACGTTT TAGGTTCACA GCAAAACTGA CCAGAAAGCA    1620
CAGAGAGGCA CTTCNATTTA CCTCCATTTA CCCCACACAG GCACATCCTC CCCTACAGAG    1680
TGGTCCATTT ATTACAGCTG CTGAACCCAC ACTGACACGC TGTTATCACT CAGAGCCTGG    1740
CAGTTTACAG AGGCTCACTC TCCGNTATGT GTCCTGTGNT TTGAACAAAT GTATAATGAC    1800
TTTATTCATT GTTTTTTAAT GAAGCTGATC TTTTCCCTCT GAAACTACAA AATGAATTTC    1860
TAGCATAGCC ATAGCAGGTG TCAAGCTATA CTACTAGGTA AATTTTAAGA AATGCCCAAC    1920
TTTATCATAT TTGCATTTCA AAATATGATT AATCACACAT AGGATTTGT  TCTTCATGC     1980
CTACAGCAAA TAGAAATAAA GTGCAAGAAA CTTTTCTGAG GCAAAGCTTT CACTTTGTGA    2040
ACGTAAAATG TTGACTCTAA TATTTTCCAT ACTGTATAT  ATGTGTGTGT ATTATGTGAG    2100
GATTCATAGT CTGCTCTTAC TTTTTTATAG TAGCTAAGAA TTATTATAAT CGCTATAAGC    2160
AGAAACAATT ATTCTTAACA AAATGAATAC ACACAAGAAA AGCTTTAGTT TAGCTATTAG    2220
AACTAACTCT ATAATTATGA TAACCATGAG ATGCTGGAAC AGGAGCCAGC AGAAGCCACA    2280
GCCCTCTGAT ATTAATATAT AAAGAAACCA AAATCTGCTT GTTAAACTGA GGCAGTTGTA    2340
```

```
TGGATACTTC AACCTGAAAA TGCCCCCTTC TTCCTGAAAC AGAACATTTA ATAAAAATGG      2400

CATGCTTGGA CAGGAATTTC TTTTTTAAAA AATGCTTAGT TTTTATG                    2447

(2) INFORMATION FOR SEQ ID NO:13:

(i) SEQUENCE CHARACTERISTICS:
        (A) LENGTH: 830 base pairs
        (B) TYPE: nucleic acid
        (C) STRANDEDNESS: single
        (D) TOPOLOGY: linear (xi) SEQUENCE DESCRIPTION: SEQ ID NO:13:

TTCCTTTATC TCCTAGATAC ACCAAGATGA AGACTGCCAC CAACATCTAC ATTTTCAACC        60

TTGCTCTGCA GATGCCTTAG CCACCAGTAC CCTGCCCTTC CAGAGTGTGA ATTACCTAAT       120

GGGAACATGG CCATTTGGAA CCATCCTTTG CAAGATAGTG ATCTCCATAG ATTACTATAA       180

CATGTTCACC AGCATATTCA CCCTCTGCAC CATGAGTGTT GATCGATACA TTGCAGTCTG       240

CCACCCTGTC AAGGCCTTAG ATTTCCGTAC TCCCCNNNNN NNNNNNNNNN NNNNNNNNNN       300

NNNNNNNNNN NNNNNNNNNN NNNNNNNNNN NNNNNNNNNN NNNNNNNNNN NNNNNNNNNN       360

NNNNNNNNGT TCCATAGATT GTACACTAAC ATTCTCTCAT CCAACCTGGT ACTGGGAAAA       420

CCTGCTGAAG ATCTGTGTTT TCATCTTCGC CTTCATTATG CCAGTGCTCA TCATTACCGT       480

GTGCTATGGA CTGATGATCT TGCGCCTCAA GAGTGTCCGC ATGCTCTCTG GCTCCAAAGA       540

AAAGGACAGG AATCTTCGAA GGATCACCAG GATGGTGCTG GTGGTGGTGG CTGTGTTCAT       600

CGTCTGCTGG ACTCCCATTC ACATTTACGT CATCATTAAA GCCTTGGTTA CAATCCCAGA       660

AACTACGTTC CAGACTGTTT CTTGGCACTT CTGCATTGCT CTAGGTTACA CAAACAGCTG       720

CCTCAACCCA GTCCTTTATG CATTTCTGGA TGAAAACTTC CACGATGCTT CAGAGAGTTC       780

TGTATCCCAA CCTCTTCCAA CATTGAGCAA CAAAACTCCA CTCGAATTCC                  830

(2) INFORMATION FOR SEQ ID NO:14:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (xi) SEQUENCE DESCRIPTION: SEQ ID NO:14:

GGGTACCGGG CCCCCCCTCG AGGTCGACGG TATCGATAAG CTTGATATCG AATTCTTACT        60

GAATTAGGTA TCTTTCTTCA CACTACTTGG TAAAAAAAAT GAAAAGGCAG AAAAATTAGC       120

CCCAAAAGAG ATGAAACTCT TCCGTCCATC ACCATTGACT CTATTGTGAA CTTATGAAAA       180

AGGTAGTTGA GCAATATGAA GGCCATGATG TGGAATTAAA CACACACACA CACACACACA       240

CACACACACA CACATGCTGG ATTCTAAATG TGTCCTTCCT CCTCTCACTC TCTTGATTCA       300

AGTTTATTTC TGAACTGAGA CACGATCACC AC                                    332

(2) INFORMATION FOR SEQ ID NO:15:

(i) SEQUENCE CHARACTERISTICS:
        (A) LENGTH: 1981 base pairs
        (B) TYPE: nucleic acid
        (C) STRANDEDNESS: single
        (D) TOPOLOGY: linear (xi) SEQUENCE DESCRIPTION: SEQ ID NO:15:

CGGATCCTTA GCATCCCCAA AGCGCCTCCG TGTACTTCTA AGGTGGGAGG GGGATACAAG        60
```

```
CAGAGGAGAA TATCGGACGC TCAGACGTTC CATTCTGCCT GCCGCTCTTC TCTGGTTCCA    120

CTAGGGCTTG TCCTTGTAAG AAACTGACGG AGCCTAGGGC AGCTGTGAGA GGAAGAGGCT    180

GGGGCGCCTG GAACCCGAAC ACTCTTGAGT GCTCTCAGTT ACAGNCTACC GAGTCCGCAG    240

GAAGCATTCA GAACCATGGA CAGCAGCGCC GGCCCAGGGA ACATCAGCGA CTGCTCTGAC    300

CCCTTAGCTC CTGCAAGTTG CTCCCCAGCA CCTGGCTCCT GGCTCAACTT GTCCCACGTT    360

GATGGAAACC AGTCCGACCC ATGCGGTCCT AACCCGACGG GCCTTGGCGG GAACGACAGC    420

CTGTGCCCTC AGACCGGCAG CCCTTCCATG GTCACAGCCA TCACCATCAT GGCCCTCTAT    480

TCTATCGTGT GTGTAGTGGG CCTCTTTGGA AACTTCCTGG TCATGTATGT GATTGTAAGA    540

TATACCAAAA TGAAGACTGC CACCAACATC TACATTTTCA ACCTTGCTCT GGCAGATGCC    600

TTAGCCACTA GCACGCTGCC CTTTCAGAGT GTTAACTACC TGATGGGAAC GTGGCCCTTT    660

GGAAACATCC TCTGCAAGAT CGTGATCTCA ATAGACTACT ACAACATGTT CACCAGTATC    720

TTCACCCTCT GCACCATGAG TGTAGACCGC TACATTGCCG TCTGCCACCC GGTCAAGGCC    780

CTGGATTTCC GTACCCCCCG AAATGCCAAA ATTGTCAATG TCTGCAACTG GATCCTCTCT    840

TCTGCCATTG GTCTGCCCGT AATGTTCATG GCAACCACAA AATACAGGCA GGGGTCCATA    900

GATTGCACCC TCACGTTCTC TCATCCCACA TGGTACTGGG AGAACCTGCT CAAAATCTGT    960

GTCTTCATCT TCGCCTTCAT CATGCCGGGC CTCATCATCA CTGTGTGTTA TGGACTGATG    1020

ATCTTACAGC TCAAGAGTGT CCGCATGCTG TCGGGCTCCA AGGAAAAGGA CAGGAACCTG    1080

CGCAGGATCA CCCGGATGGT GCTGGTGGTC GTGGCTGTAT TTATTGTCTG CTGGACCCCC    1140

ATCCACATCT ATGTCATCAT CAAAGCACTG ATCACGATTC AGAAACCAC TTTCCAGACT    1200

GTTTCCTGGC ACTTCTGCAT TGCCTTGGGT TACACAAACA GCTGCCTGAA CCCAGTTCTT    1260

TATGCGTTCC TGGATGAAAA CTTCAAACGA TGTTTTAGAG AGTTCTGCAT CCCAACTTCC    1320

TCCACAATCG AACAGCAAAA CTCTGCTCGA ATCCGTCAAA ACACTAGGGA ACACCCCTCC    1380

ACGGCTAATA CAGTGGATCG AACTAACCAC CAGCTAGAAA ATCTGGAAGC AGAAACTGCT    1440

CCATTGCCCT AACTGGGTCC CACGCCATCC AGACCCTCGC TAAACTTAGA GGCTGCCATC    1500

TACTTGGAAT CAGGTTGCTG TCAGGGTTTG TGGGAGGCTC TGGTTTCCTG GAAAAGCATC    1560

TGATCCTGCA TCATTCAAAG TCATTCCTCT CTGGCTATTC ACGCTACACG TCAGAGACAC    1620

TCAGACTGTG TCAAGCACTC AGAAGGAAGA GACTGCAGGC CACTACTGAA TCCAGCTCAT    1680

GTACAGAAAC ATCCAATGGA CCACAATACT CTGTGGTATG TGATTTGTGA TCAACATAGA    1740

AGGTGACCCT TCCCTATGTG GAATTTTTAA TTTCAAGGAA ATACTTATGA TCTCATCAAG    1800

GGAAAAATAG ATGTCACTTG TTAAATTCAC TGTAGTGATG CATAAAGGAA AAGCTACCTC    1860

TGACCTCTAG CCCAGTCACC CTCTATGGAA AGTTCCATAG GGAATATGTG AGGGAAAATG    1920

TTGCTTCCAA ATTAAATTTT CACCTTTATG TTATAGTCTA GTTAAGACAT CAGGGGCATC    1980

T                                                                    1981
```

(2) INFORMATION FOR SEQ ID NO:16:

(i) SEQUENCE CHARACTERISTICS:
        (A) LENGTH: 398 amino acids
        (B) TYPE: amino acid
        (C) STRANDEDNESS: single
        (D) TOPOLOGY: linear (xi) SEQUENCE DESCRIPTION: SEQ ID NO:16:

Met Asp Ser Ser Thr Gly Pro Gly Asn Thr Ser Asp Cys Ser Asp Pro

```
1               5                  10                 15
Leu Ala Gln Ala Ser Cys Ser Pro Ala Pro Gly Ser Trp Leu Asn Leu
            20                  25                  30
Ser His Val Asp Gly Asn Gln Ser Asp Pro Cys Gly Leu Asn Arg Thr
        35                  40                  45
Gly Leu Gly Gly Asn Asp Ser Leu Cys Pro Gln Thr Gly Ser Pro Ser
    50                  55                  60
Met Val Thr Ala Ile Thr Ile Met Ala Leu Tyr Ser Ile Val Cys Val
65                  70                  75                  80
Val Gly Leu Phe Gly Asn Phe Leu Val Met Tyr Val Ile Val Arg Tyr
                85                  90                  95
Thr Lys Met Lys Thr Ala Thr Asn Ile Tyr Ile Phe Asn Leu Ala Leu
            100                 105                 110
Ala Asp Ala Leu Ala Thr Ser Thr Leu Pro Phe Gln Ser Val Asn Tyr
        115                 120                 125
Leu Met Gly Thr Trp Pro Phe Gly Thr Ile Leu Cys Lys Ile Val Ile
    130                 135                 140
Ser Ile Asp Tyr Tyr Asn Met Phe Thr Ser Ile Phe Thr Leu Cys Thr
145                 150                 155                 160
Met Ser Val Asp Arg Tyr Ile Ala Val Cys His Pro Val Lys Ala Leu
                165                 170                 175
Asp Phe Arg Thr Pro Arg Asn Ala Lys Ile Val Asn Val Cys Asn Trp
            180                 185                 190
Ile Leu Ser Ser Ala Ile Gly Leu Pro Val Met Phe Met Ala Thr Thr
        195                 200                 205
Lys Tyr Arg Gln Gly Ser Ile Asp Cys Thr Leu Thr Phe Ser His Pro
    210                 215                 220
Thr Trp Tyr Trp Glu Asn Leu Leu Lys Ile Cys Val Phe Ile Phe Ala
225                 230                 235                 240
Phe Ile Met Pro Ile Leu Ile Ile Thr Val Cys Tyr Gly Leu Met Ile
                245                 250                 255
Leu Arg Leu Lys Ser Val Arg Met Leu Ser Gly Ser Lys Glu Lys Asp
            260                 265                 270
Arg Asn Leu Arg Arg Ile Thr Arg Met Val Leu Val Val Val Ala Val
        275                 280                 285
Phe Ile Val Cys Trp Thr Pro Ile His Ile Tyr Val Ile Ile Lys Ala
    290                 295                 300
Leu Ile Thr Ile Pro Glu Thr Thr Phe Gln Thr Val Ser Trp His Phe
305                 310                 315                 320
Cys Ile Ala Leu Gly Tyr Thr Asn Ser Cys Leu Asn Pro Val Leu Tyr
                325                 330                 335
Ala Phe Leu Asp Glu Asn Phe Lys Arg Cys Phe Arg Glu Phe Cys Ile
            340                 345                 350
Pro Thr Ser Ser Thr Ile Glu Gln Gln Asn Ser Thr Arg Val Arg Gln
        355                 360                 365
Asn Thr Arg Glu His Pro Ser Thr Ala Asn Thr Val Asp Arg Thr Asn
    370                 375                 380
His Gln Leu Glu Asn Leu Glu Ala Glu Thr Ala Pro Leu Pro
385                 390                 395
```

(2) INFORMATION FOR SEQ ID NO:17:

(i) SEQUENCE CHARACTERISTICS:
        (A) LENGTH: 376 amino acids (B) TYPE: amino acid
(C) STRANDEDNESS: single
(D) TOPOLOGY: linear (xi) SEQUENCE DESCRIPTION: SEQ ID NO:17:

```
Met Glu Ser Pro Ile Gln Ile Phe Arg Gly Asp Pro Gly Pro Thr Cys
 1               5                  10                  15

Ser Pro Ser Ala Cys Leu Leu Pro Asn Ser Ser Trp Phe Pro Asn
             20                  25                  30

Trp Ala Glu Ser Asp Ser Asn Gly Ser Val Gly Ser Glu Asp Gln Gln
             35                  40                  45

Leu Glu Ser Ala His Ile Ser Pro Ala Ile Pro Val Ile Ile Thr Ala
     50                  55                  60

Val Tyr Ser Val Val Phe Val Val Gly Leu Val Gly Asn Ser Leu Val
 65                  70                  75                  80

Met Phe Val Ile Ile Arg Tyr Thr Lys Met Lys Thr Ala Thr Asn Ile
                 85                  90                  95

Tyr Ile Phe Asn Leu Ala Leu Ala Asp Ala Leu Val Thr Thr Thr Met
                100                 105                 110

Pro Phe Gln Ser Ala Val Tyr Leu Met Asn Ser Trp Pro Phe Gly Asp
            115                 120                 125

Val Leu Cys Lys Ile Val Ile Ser Ile Asp Tyr Tyr Asn Met Phe Thr
130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
                165                 170                 175

Ile Ile Asn Ile Cys Ile Trp Leu Leu Ala Ser Ser Val Gly Ile Ser
            180                 185                 190

Ala Ile Val Leu Gly Gly Thr Lys Val Arg Glu Asp Val Ile Glu Cys
            195                 200                 205

Ser Leu Gln Phe Pro Asp Asp Glu Trp Trp Asp Leu Phe Met Lys Ile
    210                 215                 220

Cys Val Phe Val Phe Ala Phe Val Ile Pro Val Leu Ile Ile Ile Val
225                 230                 235                 240

Cys Tyr Thr Leu Met Ile Leu Arg Leu Lys Ser Val Arg Leu Leu Ser
                245                 250                 255

Gly Ser Arg Glu Lys Asp Arg Asn Leu Arg Arg Ile Thr Lys Leu Val
            260                 265                 270

Leu Val Val Val Ala Val Phe Ile Ile Cys Trp Thr Pro Ile His Ile
    275                 280                 285

Phe Ile Leu Val Glu Ala Leu Gly Ser Thr Ser His Ser Thr Ala Ala
    290                 295                 300

Leu Ser Ser Tyr Tyr Phe Cys Ile Ala Leu Gly Tyr Thr Asn Ser Ser
305                 310                 315                 320

Leu Asn Pro Val Leu Tyr Ala Phe Leu Asp Glu Asn Phe Lys Arg Cys
            325                 330                 335

Phe Arg Asp Phe Cys Phe Pro Ile Lys Met Arg Met Glu Arg Gln Ser
            340                 345                 350

Thr Asn Arg Val Arg Asn Thr Val Gln Asp Pro Ala Ser Met Arg Asp
            355                 360                 365

Val Gly Gly Met Asn Lys Pro Val
370                 375
```

```
(2) INFORMATION FOR SEQ ID NO:18:

(i) SEQUENCE CHARACTERISTICS:
        (A) LENGTH: 5 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 5
        (D) OTHER INFORMATION: /note= "Any amino acid"

(xi) SEQUENCE DESCRIPTION: SEQ ID NO:18:

Tyr Gly Gly Phe Xaa
1               5
```

OPIOID RECEPTOR GENES

This application is filed under 35 U.S.C. § 371 as a national phase of PCT/US93/07665 filed Aug. 13, 1993 which is a continuation-in-part of U.S. Ser. No. 07/929,200 filed Aug. 13, 1992, now abandoned.

This invention was made with Government support under Grant No. DA05010 awarded by the Alcohol, Drug Abuse and Mental Health Administration. The Government has certain rights in the invention.

TECHNICAL FIELD

The invention relates to substances involved in vertebrate nervous systems, and in particular to the opioid receptors and activities mediated thereby. Accordingly, the invention concerns recombinant materials useful for the production of opioid receptors, the receptor as a diagnostic tool, therapeutic and diagnostic compositions relevant to the receptor, and methods of using the receptor to screen for drugs that modulate the activity of the receptor.

BACKGROUND ART

The term "opioid" generically refers to all drugs, natural and synthetic, that have morphine-like actions. Formerly, the term "opiate" was used to designate drugs derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources have continued to use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce their major effects on the central nervous and digestive systems. The effects are diverse, including analgesia, drowsiness, mood changes, respiratory depression, dizziness, mental clouding, dysphoria, pruritus, increased pressure in the biliary tract, decreased gastrointestinal motility, nausea, vomiting, and alterations of the endocrine and autonomic nervous systems.

A significant feature of the analgesia produced by opioids is that it occurs without loss of consciousness. When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

The development of tolerance and physical dependence with repeated use is a characteristic feature of all opioid drugs, and the possibility of developing psychological dependence on the effect of these drugs is a major limitation for their clinical use. There is evidence that phosphorylation may be associated with tolerance in selected cell populations (Louie, A. et al. *Biochem Biophys Res Comm* (1988) 152:1369–75).

Acute opioid poisoning may result from clinical overdosage, accidental overdosage, or attempted suicide. In a clinical setting, the triad of coma, pinpoint pupils, and depressed respiration suggest opioid poisoning. Mixed poisonings including agents such as barbiturates or alcohol may also contribute to the clinical picture of acute opioid poisoning. In any scenario of opioid poisoning, treatment must be administered promptly.

The opioids interact with what appear to be several closely related receptors. Various inferences have been drawn from data that have attempted to correlate pharmacologic effects with the interactions of opioids with a particular constellation of opioid receptors (Goodman and Gilman's, THE PHARMACOLOGICAL BASIS OF THERAPEUTICS, 7th ed, pp. 493–95 (MacMillan 1985)). For example, analgesia has been associated with mu and kappa receptors. Delta receptors are believed to be involved in alterations of affective behavior, based primarily on the localization of these receptors in limbic regions of the brain. Additionally, activation, e.g., ligand binding with stimulation of further receptor-mediated responses, of delta opioid receptors is believed to inhibit the release of other neurotransmitters. The pathways containing relatively high populations of delta opioid receptor are similar to the pathways implicated to be involved in Huntington's disease. Accordingly, it is postulated that Huntington's disease may correlate with some effect on delta opioid receptors.

Two distinct classes of opioid molecules can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., *Science* (1973) 179:1011–1014), the differential pharmacological and physiological effects of both opioid peptide analogues and alkaloid opiates served to delineate multiple opioid receptors. Accordingly, three anatomically and pharmacologically distinct opioid receptor types have been described: delta, kappa and mu. Furthermore, each type is believed to have sub-types (Wollemann, M., *J. Neurochem.* (1990) 54:1095–1101; Lord, J. A., et al., *Nature* (1977) 267:495–499).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: *Biological Basis of Substance Abuse*, S. G. Korenman & J. D. Barchas, eds., Oxford University Press (in press); North, A. R., et al., *Proc Natl Acad Sci USA* (1990) 87:7025–29; Gross, R. A., et al., *Proc Natl Acad Sci USA* (1990) 87:7025–29; Sharma, S. K., et al., *Proc Natl Acad Sci USA* (1975) 72:3092–96). Although the functional mechanisms are the same, the behavioral manifestations of receptor-selective drugs differ greatly (Gilbert, P. E. & Martin, W. R., *J Pharmacol Exp Ther* (1976) 198:66–82). Such differences may be attributable in part to the anatomical location of the different receptors.

Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex (Mansour, A., et al., *Trends in Neurosci* (1988) 11:308–14). The rat cerebellum is remarkably devoid of opioid receptors including delta opioid receptors.

Several opioid molecules are known to selectively or preferentially bind delta receptors. Of the vertebrate endogenous opioids, the enkephalins, particularly met-enkephalin (SEQ ID NO:1) and leu-enkephalin (SEQ ID NO:2), appear to possess the highest affinity for delta receptors, although the enkephalins also have high affinity for mu receptors. Additionally, the deltorphans, peptides isolated from frog skin, comprise a family of opioid peptides that have high affinity and selectivity for delta receptors (Erspamer, V., et al., *Proc Natl Acad Sci USA* (1989) 86:5188–92).

A number of synthetic enkephalln analogues are also delta receptor-selective including (D-Ser$^2$) leucine enkephalin Thr (DSLET) (SEQ ID NO:3) (Garcel, G. et al. (1980) *FEBS. Lett*. 118:245–247) and (D-Pen$^2$, D-Pen$^5$) enkephalin (DPDPE) (SEQ ID NO:4) (Akiyama, K. et al., *Proc. Natl. Acad. Sci. USA* (1985) 82:2543–2547).

Recently a number of other selective delta receptor ligands have been synthesized, and their bioactivities and binding characteristics suggest the existence of more than one delta receptor subtype (Takemori, A. E., et al., *Ann. Rev. Pharm. Toxicol*., (1992) 32:239–69; Negri, L., et al., *Eur J Pharmacol* (1991) 196:355–335; Sofuoglu, M., et al., *Pharmacolocrist* (1990) 32:151).

Although the synthetic pentapeptide 2dAla, 5dLeu enkephalin (DADLE) (SEQ ID NO:5) was considered to be delta-selective, it also binds equally well to mu receptors. The synthetic peptide D-Ala$^2$-N-Me-Phe$^4$-Gly-ol$^5$-enkephalin (DAGO) (SEQ ID NO:6) has been found to be a selective ligand for mu-receptors.

The existence of multiple delta opioid receptors has been implied not only from the pharmacological studies addressed above, but also from molecular weight estimates obtained by use of irreversible affinity ligands. Molecular weights for the delta opioid receptor that range from 30 kDa to 60 kda (Evans, C. J., supra; Evans, C. J. et al., *Science* 258:1952–1955 (1992), which document corresponds to the dislcosure of the priority document of the present application; Bochet, P. et al., *Mol Pharmacol* (1988) 34:436–43). The various receptor sizes may represent alternative splice products, although this has not been established.

Many studies of the delta opioid receptor have been performed with the neuroblastoma/glioma cell line NG108-15, which was generated by fusion of the rat glial cell line (C6BU-1) and the mouse neuroblastoma cell line (N18-TG2) (Klee, W. A. and Nirenberg, M. A., *Proc. Natl. Acad. Sci. USA* (1974) 71:3474–3477). The rat glial cell line expresses essentially no delta opioid receptors, whereas the mouse neuroblastoma cell line expresses low amounts of the receptor. Thus, it has been suggested that the delta receptor in the NG108-15 cells is of mouse chromosomal origin (Law, *Mol Pharm* (1982) 21:438–91). Each NG108-15 cell is estimated to express approximately 300,000 delta-receptors. Only delta-type opioid receptors are expressed, although it is not known whether these represent more than a single subtype. Thus, the NG108-15 cell line has served to provide considerable insight into the binding characterization of opioid receptors, particularly delta opioid receptors. However, the NG108-15 cell line is a cancer-hybrid and may not be completely representative of the delta receptor in endogenous neurons due to the unique cellular environment in the hybrid cells.

An extensive literature has argued that the opioid receptors are coupled to G-proteins (see, e.g., Schofield, P. R., et al., *EMBO J*., 8:489–95 (1989)), and are thus members of the family of G-protein coupled receptors. G-proteins are guanine nucleotide binding proteins that couple the extracellular signals received by cell surface receptors to various intracellular second messenger systems. Identified members of the G-protein-coupled family share a number of structural features, the most highly conserved being seven apparent membrane-spanning regions, which are highly homologous among the members of this family (Strosberg, A. D., *Eur. J. Biochem*. 196:1–10 (1991)). Evidence that the opioid receptors are members of this family includes the stimulation of GTPase activity by opioids, the observation that GTP analogues dramatically effect opioid and opiate agonist binding, and the observation that pertussis toxin (which by ADP ribosylation selectively inactivates both the Gi and Go subfamilies of G-proteins) blocks opioid receptor coupling to adenylate cyclase and to K$^+$ and Ca$^{2+}$ channels (Evans, C. J., supra).

The members of the G-protein-coupled receptor family exhibit a range of characteristics. Many of the G-protein-coupled receptors, e.g., the somatostatin receptor and the angiotensin receptor, have a single exon that encodes the entire protein coding region (Strosberg supra; Langord, K., et al., *Biochem. Biophys. Res. Comm*. 138:1025–1032 (1992)). However, other receptors, such as substance P receptor and the dopamine D2 receptor, contain the protein coding region. The D2 receptor is particularly interesting in that alternate splicing of the gene gives rise to different transcribed products (i.e., receptors) (Evans, C. J., supra; Strosberg, supra). Interestingly, somatostatin ligands are reported to bind to opioid receptors (Terenius, L., *Eur. J. Pharmacol*. 38:211 (1976); Mulder, A. H., et al., *Eur. J. Pharmacol*. 205:1–6 (1991)) and, furthermore, to have similar molecular mechanisms (Tsunoo, A., et al., *Proc. Natl. Acad. Sci. USA* 83:9832–9836 (1986)).

In previous efforts to describe and purify opioid receptors, two clones have been described that were hypothesized either to encode a portion of or entire opioid receptors. The first clone, which encodes the opiate binding protein OBCAM (Schofield et al., supra), was obtained by utilizing a probe designed from an amino acid sequence of a protein purified on a morphine affinity column. OBCAM lacks any membrane spanning domains but does have a C-terminal domain that is characteristic of attachment of the protein to the membrane by a phosphatidylinositol (PI) linkage. This feature, which is shared by members of the immunoglobulin superfamily, is not common to the family of receptors coupled to G-proteins. Thus, it has been proposed that OBCAM is part of a receptor complex along with other components that are coupled to G-proteins (Schofield et al., supra). At present, however, there is no direct evidence for such a complex.

A second proposed opioid receptor clone was obtained in an effort to clone a receptor that binds kappa opioid receptor ligands (Xie, G. X., *Proc Natl Acad Sci USA* 89:4124–4128 (1992)). A DNA molecule encoding a G-coupled receptor from a placental cDNA library was isolated. This receptor has an extremely high homology with the neurokinin B receptor (84% identical throughout the proposed protein sequence). When this clone was expressed in COS cells, it displayed opioid peptide displaceable binding of $^3$H-bremazocine (an opiate ligand with high affinity for kappa receptors). However, the low affinity of this receptor for $^3$H-bremazocine, and the lack of appropriate selectivity since this receptor (binding both mu and delta ligands) made it doubtful that this cloned molecule is actually an opioid receptor.

Furthermore, characterization of opioid receptor proteins has proven difficult because of their instability once solubilized from the membrane; purified delta opioid receptors have not been isolated. The previous estimates of opioid receptor molecular weights ranging from 30 kDa to 60 Kda further reflect the difficulty in isolating and characterizing these proteins.

Recently, DNA encoding the murine kappa and delta opioid receptors from mouse brain was reported by Yasuda, K. et al. *Proc Natl Acad Sci USA* (1993) 90:6736–6740. The sequence of the clones indicated the presence of the expected seven transmembrane regions. In addition, Chen, Y. et al. in a soon-to-be-published manuscript in *Molecular Pharmacology* (1993) report the "molecular cloning and functional expression of a mu opioid receptor from rat brain". In fact, the rat mu receptor was cloned using the present inventors' DOR-1 clone, which lends enabling support to the present invention disclosed below. Finally, the mouse delta opioid receptor was disclosed as having been cloned (Kieffer, B. J. et al., *Proc. Natl. Acad. Sci. USA* 89:12048–12052 (1992 Dec.) after the filing date of the priority document of the present application. However, the sequence reported therein differs from the sequence reported by the present inventors for the mouse delta receptor (Evans et al., 1992, supra; this disclosure).

DISCLOSURE OF THE INVENTION

The present invention provides recombinant nucleic acid molecules which encode the murine delta opioid receptor, as well as recombinant nucleic acid molecules which can be retrieved using low-stringency hybridization to this disclosed DNA. Thus, the invention provides genes encoding the delta, kappa and mu receptors of any species containing genes encoding such receptors sufficiently homologous to hybridize under low-stringency conditions described herein.

Thus, in one aspect, the invention is directed to recombinant nucleic acid molecules and methods for the production of an opioid receptor wherein the opioid receptor is encoded by a gene which hybridizes under low-stringency to the nucleotide sequence of FIG. 5 (SEQ ID NO:7) or to its complement. By "low-stringency" is meant 50% formamide/6×SSC, overnight at 37° C. for the hybridization, followed by washes at 2×SSC 0.1% SDS at room temperature.

Also provided are expression systemsd comprising the nucleic acid molecules described above. The receptor can be recombinantly produced using these expression systems and host cells modified to contain them.

Especially useful are vertebrate cells which express the opioid receptor gene so that the opioid receptor protein is displayed at the surface of the cells. These cells offer means to screen native and synthetic candidate agonists and antagonists for the opioid receptors.

In still other aspects, the invention is directed to methods to screen candidate agonists and/or antagonists acting at opioid receptors using the recombinant transformed cells of the invention. Such assays include (1) binding assays using competition with ligands known to bind opioid receptors, (2) agonist assays which analyze activation of the secondary pathways associated with opioid receptor activation in the transformed cells, and (3) assays which evaluate the effect on binding of the candidate to the receptor by the presence or absence of sodium ion and GTP. Antagonist assays include the combination of the ability of the candidate to bind the receptor while failing to effect further activation, and, more importantly, competition with a known agonist.

Still another aspect of the invention is provision of antibody compositions which are immunoreactive with the opioid receptor proteins. Such antibodies are useful, for example, in purification of the receptors after solubilization or after recombinant production thereof.

In still other aspects, the invention is directed to probes useful for the identification of DNA which encodes related opioid receptors in various species or different types and subtypes of opioid receptors.

Accordingly, an object of the present invention is to provide an isolated and purified form of a DNA sequence encoding an opioid receptor, which is useful as a probe as well as in the production of the receptor.

Another object is to provide a recombinantly produced DNA sequence encoding an opioid receptor.

Another object is to produce an antisense sequences corresponding to known sense sequences encoding the opioid receptors.

Another object of the invention is to provide a DNA construct comprised of a control sequence operatively linked to a DNA sequence which encodes an opioid receptor and to provide recombinant host cells modified to contain the DNA construct.

Another object is to isolate, clone and characterize, from various vertebrate species, DNA sequences encoding the various related receptors, by hybridization of the DNA derived from such species with a native DNA sequence encoding the opioid receptor of the invention.

An advantage of the present invention is that opioid receptor-encoding DNA sequences can be expressed at the surface of host cells which can conveniently be used to screen drugs for their ability to interact with and/or bind to the receptors.

These and other objects, advantages and features of the present invention will become apparent to those persons skilled in the art.

BRIEF DESCRIPTION OF THE DRAWINGS

FIG. 5 shows the nucleotide sequence (SEQ ID NO:7) and the deduced amino acid sequence (SEQ ID NO:8) of the DOR-1 clone.

FIG. 6 depicts the deduced amino acid sequence of DOR-1(SEQ ID NO:8), compared with the rat somatostatin receptor (SEQ ID NO:9). Consensus glycosylation sites predicted to fall in extracellular domains are indicated by an asterisk. Potential protein kinase C sites are listed in Example 5. The seven predicted membrane spanning regions (underlined) are predicted based on the hydrophobicity profile and published predictions (Macvector software program (IBI); T. Hopp, and K. Woods, *Proc Natl Acad Sci USA* 78:3842–3828 (1981)). For sequencing, the cDNA insert was subcloned into pBluescript and both strands were sequenced from single-stranded DNA using Sequenase and Taq cycle sequencing. For ambiguities due to compressions 7-deaza-dGTP replaced dGTP in the sequencing reactions and the products were resolved on formamide gels.

FIG. 8a (SEQ ID NO:10 and SEQ ID NO:11) shows a partial nucleotide sequence of the human delta opioid receptor genomic clone H3 (also designated human DORa or hDORa).

FIG. 8b (SEQ ID NO:12) shows a partial nucleotide sequence of the human kappa opioid receptor genomic clone H14 (also designated human KORa or hKORa).

FIG. 8c (SEQ ID NO:13) shows a partial nucleotide sequence of the human mu opioid receptor genomic clone H20 (also designated human MORa or hMORa).

FIG. 8d (SEQ ID NO:14) shows the nucleotide sequence of the CACACA repeat near the H20 DNA.

FIG. 9 (SEQ ID NO:15) shows the nucleotide sequence of the murine mu-receptor clone DOR-2 also named mMOR-1 or mMOR-1α.

FIG. 10 (SEQ ID NO:8 and SEQ ID NO:16 and SEQ ID NO:17) shows the homology of various receptor amino acid sequences.

MODES OF CARRYING OUT THE INVENTION

Figure 1:
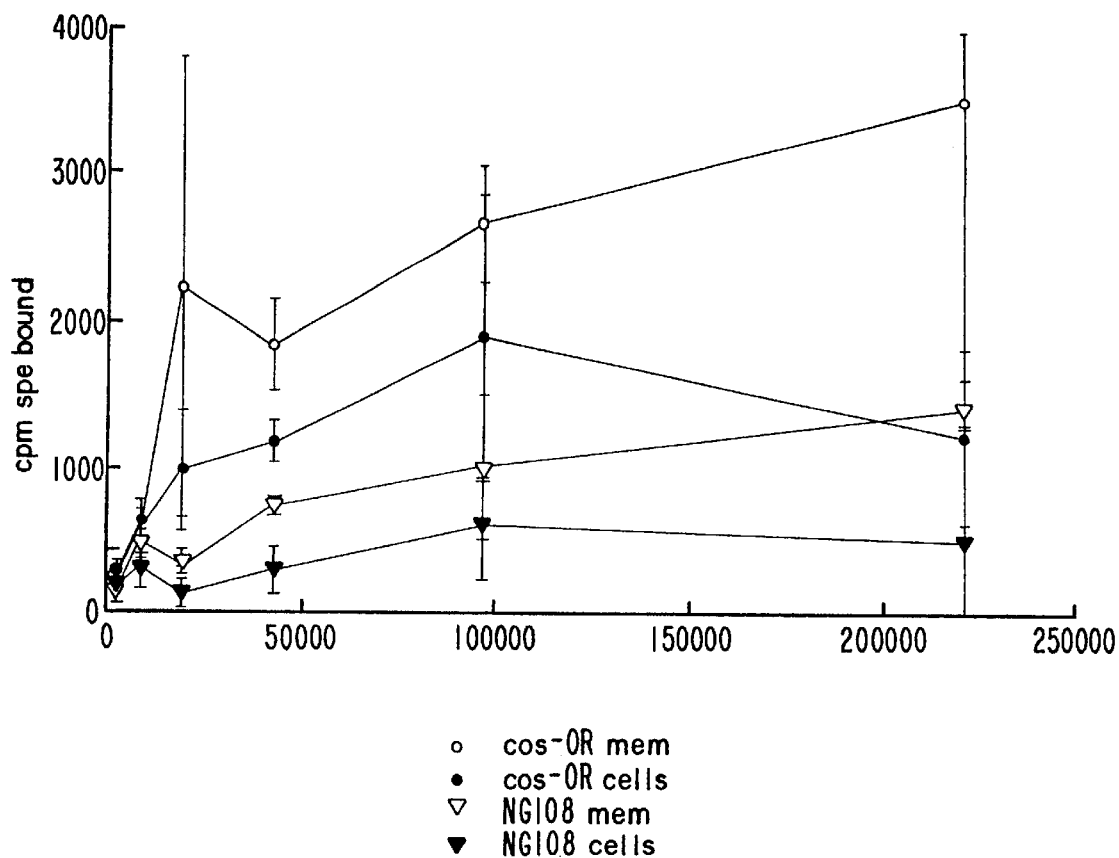
FIG. 1 depicts a comparison of binding of $^3$H-diprenorphine (saturation curves) between NG108-15 cells and COS cells three days following transfection (by electroporation) of each with DOR-1 in the CDM8 vector. Specific opioid binding was undetectable in nontransfected COS cells or COS cells transfected with plasmid alone.

The invention provides DNA encoding mammalian opioid receptor protein and additional recombinant nucleic acids, expression vectors and methods useful for the production of these proteins. In addition, eucaryotic cells, such as COS cells, transformed with the recombinant molecules of the invention so as to express opioid receptor proteins at their surface are useful in screening assays to identify candidate opioid agonists and antagonists. In addition, antibodies may be raised to the recombinantly produced opioid receptor proteins. These antibodies are useful in immunoassays for said protein and in affinity purification thereof.

Recombinant Opioid Receptor

Illustrated hereinbelow is the obtention of a cDNA encoding a murine delta opioid receptor. The complete DNA sequence of the cDNA, and the amino acid sequence encoded thereby, are set forth herein in FIG. 5. The availability of this cDNA permits the retrieval of the corresponding opioid receptor-encoding DNA from other vertebrate species. Accordingly, the present invention places within the possession of the art, recombinant molecules and methods for the production of cells expressing opioid receptors of various types and of various vertebrate species. Thus, the cDNA of FIG. 5, or a portion thereof, may be used as a probe to identify that portion of vertebrate genomic DNA or cDNA which encodes an opioid receptor protein. Illustrative methods used to prepare a genomic library and identify the opioid receptor-encoding genes are described for convenience hereinbelow.

The DOR-1 clone described in FIG. 5 is a cDNA clone corresponding to the murine delta opioid receptor. The present inventors found, and describe herien, that screening of a human genomic library under conditions of low stringency results in the recovery of DNA encoding all three types of human opioid receptors. Similarly, a murine genomic clone was obtained. In addition, a cDNA clone was obtained from a mouse brain library encoding the murine mu opioid receptor. Thus, either cDNA libraries from appropriate sources, such as brain, or genomic libraries, are fruitful sources or substrates for obtaining the DNA of the present invention and the corresponding recombinant materials. The invention is thus directed to DNA encoding an opioid receptor of a vertebrate, wherein the opioid receptor is encoded by a nucleotide sequence which hybridizes under conditions of low stringency to the nucleotide sequence shown in FIG. 5 or to its complement.

In the alternative, the DNA of FIG. 5 or a portion thereof may be used to identify specific tissues or cells which express opioid receptor protein by analyzing the mRNA, for example, using Northern blot techniques. Those tissues which are identified as containing mRNA encoding opioid receptor protein using the probes of the invention are then suitable sources for preparation of cDNA libraries which may further be probed using the cDNA described hereinbelow.

The DNA encoding the various vertebrate opioid receptor proteins, obtained in general as set forth above, according to the standard techniques described hereinbelow, can be used to produce cells which express the opioid receptor at their surface; such cells are typically eucaryotic cells, in particular, mammalian cells such as COS cells or CHO cells. Suitable expression systems in eucaryotic cells for such production are described hereinbelow. The opioid receptor proteins may also be produced in procaryotes or in alternative eucaryotic expression systems for production of the protein per se. The DNA encoding the protein may be ligated into expression vectors preceded by signal sequences to effect its secretion, or may be produced intracellularly, as well as at the cell surface, depending on the choice of expression system and host. If desired, the opioid receptor protein thus recombinantly produced may be purified using suitable means of protein purification, and, in particular, by affinity purification using antibodies or fragments thereof immunospecific for the opioid receptor protein.

Screening for Opioid Agonists and Antagonists Using Recombinant Cells

The ability of a candidate compound to act as an opicid agonist or antagonist may be assessed using the recombinant cells of the invention in a variety of ways. To exhibit either agonist or antagonist activity, the candidate compound must bind to the opioid receptor. Thus, to assess the ability of the candidate to bind, either a direct or indirect binding assay may be used. For a direct binding assay, the candidate binding compound is itself detectably labeled, such as with a radioisotope or fluorescent label, and binding to the recombinant cells of the invention is assessed by comparing the acquisition of label by the recombinant cells to the acquisition of label by corresponding untransformed (control) cells.

More convenient, however, is the use of a competitive assay wherein the candidate compound competes for binding to the recombinant cells of the invention with a detectably labeled form of an opioid ligand known to bind to the receptor. Such ligands are themselves labeled using radioisotopes or fluorescent moieties, for example. A particularly suitable opioid known to bind to this receptor is diprenorphine. A typical protocol for such an assay is as follows:

In general, about $10^6$ recombinant cells are incubated in suspension in 1.0 ml of Kreb's Ringer Hepes Buffer (KRHB) at pH 7.4, 37° C. for 20 min with $^3$H-diprenorphine.

Nonspecific binding is determined by the addition of 400 nM diprenorphine in the binding mixtures. Various concentrations of candidate compounds are added to the reaction mixtures. The incubations are terminated by collecting the cells on Whatman GF-B filters, with removal of excess radioactivity by washing the filters three times with 5 ml of KRHB at 0° C. After incubating at 20° C. overnight in 5 ml of scintillation fluid, such as Liquiscint (National Diagnostics, Somerville, N.J.), the radioactivity on the filters is determined by liquid scintillation counting.

The $K_d$ (dissociation constant) values for the candidate opiate ligands can be determined from the $IC_{50}$ value ("inhibitory concentration$_{50}$" means the concentration of candidate ligand that results in a 50% decrease in binding of labeled diprenorphine).

The effects of sodium and GTP on the binding of ligands to the recombinantly expressed receptors can be used to distinguish agonist from antagonist activities. If the binding of a candidate compound is sensitive to $Na^+$ and GTP, it is more likely to be an agonist than an antagonist, since the functional coupling of opioid receptors to second messenger molecules such as adenylate cyclase requires the presence of both sodium and GTP (Blume et al., *Proc. Natl. Acad. Sci. USA* 73:26–35 (1979)). Furthermore, sodium, GTP, and GTP analogues have been shown to effect the binding of opioids and opioid agonists to opioid receptors (Blume, *Life Sci* 22:1843–52 (1978)). Since opioid antagonists do not exhibit binding that is sensitive to guanine nucleotides and sodium, this effect is used as a method for distinguishing agonists from antagonists using binding assays.

In addition, agonist activity can directly be assessed by the functional result within the cell. For example, it is known that the binding of opioid agonists inhibits cAMP formation, inhibits potassium channel activation, inhibits calcium channel activation, and stimulates GTPase. Assessment of these activities in response to a candidate compound is diagnostic of agonist activity. In addition, the ability of a compound to interfere with the activating activity of a known agonist such as etorphine effectively classifies it as an antagonist.

In one typical assay, the measurement of cAMP levels in cells expressing opioid receptors is carried out by determining the amount of $^3$H-cAMP formed from intracellular ATP pools prelabeled with $^3$H-adenine (Law et al., supra). Thus, cAMP formation assays are carried out with $0.5 \times 10^6$ cells/0.5 ml of KRHB at pH 7.4, incubated at 37° C. for 20 minutes. After addition of the internal standard $^{32}$P-cAMP, the radioactive cAMP is separated from other $^3$H-labeled nucleotides by known double-column chromatographic methods. The opiate agonists' ability to inhibit cAMP accumulation is then determined as described by Law et al. (supra).

The potency of a candidate opiate antagonist can be determined by measuring the ability of etorphine to inhibit cyclic AMP accumulation in the presence and in the absence of known amounts of the candidate antagonist. The inhibition constant ($K_i$) of an antagonist can then be calculated from the equation for competitive inhibitors.

An interesting feature of screening assays using the prior art NG108-15 cells is that the agonist adenylate cyclase inhibition function apparently does not require binding of all receptors on these cells.

Thus, the $K_d$ and $K_i$ values for the opioid ligands differed when using these cells.

The foregoing assays, as described above, performed on the recombinantly transformed cells of the present invention, provide a more direct and more convenient screen for candidate compounds having agonist and antagonist opioid receptor activity than that previously available in the art. Furthermore, such assays are more sensitive since cells can, in accordance with the present invention, be engineered to express high levels of the opioid receptor. Additionally, cells engineered in accordance with the present invention will circumvent the concern that NG108-15 cells, due to their tumor cell background, have a cellular environment that artifactually affects opioid receptor expression.

The mu opioid encoding DNA described herein also offer a means to follow inheritance patterns. DNA sequence polymorphisms frequently occur in the noncoding regions that surround genes. Polymorphisms are especially frequent in repeat sequences such as CACACA which often show distinct polymorphisms in the number of repeats that are present in different individuals. These polymorphisms offer a marker by which to follow the inheritance of the gene among family members. The inheritance of a gene (such as MORa) or its human counterpart can be followed by polymerase chain reaction (PCR) amplification of the region surrounding the CACACA polymorphism and analyzing the resulting products. This would be a useful diagnostic marker for the mu opioid receptor gene.

Methods to Preoare Opioid Receptor Protein or Portions Thereof

The present invention provides the amino acid sequence of a murine opioid receptor; similarly, the availability of the cDNA of the invention places within possession of the art corresponding vertebrate opioid receptors whose amino acid sequence may also be determined by standard methods. As the amino acid sequences of such opioid receptors are known, or determinable, in addition to purification of such receptor protein from native sources, recombinant production or synthetic peptide methodology may also be employed for producing the receptor protein or peptide.

The opioid receptor or portions thereof can thus also be prepared using standard solid phase (or solution phase) peptide synthesis methods, as is known in the art. In addition, the DNA encoding these peptides may be synthesized using commercially available oligonucleotide synthesis instrumentation for production of the protein in the manner set forth above. Production using solid phase peptide synthesis is, of course, required if amino acids not encoded by the gene are to be included.

The nomenclature used to describe the peptides and proteins of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $NH3^+$ and C-terminal $COO^-$ at physiological pH are understood to be present though not necessarily specified and shown, either in specific examples or in generic formulas. Free functional groups on the side chains of the amino acid residues may also be modified by glycosylation, phosphorylation, cysteine binding, amidation, acylation or other substitution, which can, for example, alter the physiological, biochemical, or biological properties of the compounds without affecting their activity within the meaning of the appended claims.

In the peptides shown, each gene-encoded residue, where appropriate, is represented by a single letter designation, corresponding to the trivial name of the amino acid, in accordance with the following conventional list:

| Amino Acid | One-Letter Symbol | Three-letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Nomenclature of Enkephalins

Enkephalins are either of two peptides having five residues with the N-terminal residue numbered 1:

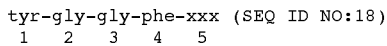
```
tyr-gly-gly-phe-xxx  (SEQ ID NO:18)
 1   2   3   4   5
```

In "met enkephalin" the fifth residue is methionine:
  tyr-gly-gly-phe-met (SEQ ID NO:1)
In "leu enkephalin" the 5th residue is leucine:
  tyr-gly-gly-phe-leu (SEQ ID NO:2)
Enkephalin analogs can be made with (1) amino acid substitutions, (2) D-amino acid substitutions, and/or (3) additional amino acids. The site at which the substitution is made is noted at the beginning of the compound name. For example, "(D-ala$^2$, D-leu$^5$) enkephalin" means that D-ala is present at the second position and D-leu is present at the fifth position:
  tyr-[D-ala]-gly-phe-[D-leu] (SEQ ID NO:5)
One letter abbreviations can also be used. Thus, "(D-ser$^2$) leu enkephalin" could be abbreviated as "DSLE." Additional residues are noted as well. Thus, the addition of a threonine residue (to the sixth position) of (D-ser$^2$) leu enkephalin would be "(D-ser$^2$) leu enkephalin thr" which could be abbreviated as "DSLET":
  tyr-[D-ser]-gly-phe-leu-thr (SEQ ID NO:3)

Antibodies

Antibodies immunoreactive with the opioid receptor protein or peptide of the present invention can be obtained by immunization of suitable mammalian subjects with peptides, containing as antigenic regions those portions of the receptor intended to be targeted by the antibodies. Certain protein sequences have been determined to have a high antigenic potential. Such sequences are listed in antigenic indices, for example, MacVector software (I.B.I.) Thus, by determining the sequence of the opioid receptor protein and evaluating the sequence with an antigenic index, probable antigenic sequences are located.

Antibodies are prepared by immunizing suitable mammalian hosts according to known immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended or interspersed with cysteine residues, for example, to facilitate linking to carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal antibody (mAb) preparations is preferred. Immortalized cell lines which secrete the desired mabs may be prepared using the standard method of Kohler and Milstein or modifications which effect immortalization of lymphocytes or spleen cells, as is generally known. The immortalized cell lines secreting the desired mAbs are screened by immunoassay in which the antigen is the peptide hapten or is the opioid receptor itself displayed on a recombinant host cell. When the appropriate immortalized cell culture secreting the desired mAb is identified, the cells can be cultured either in vitro or by intraperitoneal injection into animals wherein the mAbs are produced in the ascites fluid.

The desired mAbs are then recovered from the culture supernatant or from the ascites fluid. In addition to intact antibodies, fragments of the mAbs or of polyclonal antibodies which contain the antigen-binding portion can be used as antagonists. Use of immunologically reactive antigen binding fragments, such as the Fab, Fab', of F(ab')$_2$ fragments, is often preferable, especially in a therapeutic context, as these fragments are generally less immunogenic than the whole immunoglobulin molecule.

Standard Methods

The techniques for sequencing, cloning and expressing DNA sequences encoding the amino acid sequences corresponding to a opioid receptor, e.g., polymerase chain reaction (PCR), synthesis of oligonucleotides, probing a cDNA library, transforming cells, constructing vectors, preparing antisense oligonucleotide sequences based on known sense nucleotide sequences, extracting messenger RNA, preparing cDNA libraries, and the like are well-established in the art. Ordinarily skilled artisans are familiar with the standard resource materials, specific conditions and procedures. The following paragraphs are provided for convenience, it being understood that the invention is limited only by the appended claims.

RNA Preparation and Northern Blot

RNA preparation is as follows: The samples used for preparation of RNA are immediately frozen in liquid nitrogen and then stored until use at −80° C. The RNA is prepared by CsCl centrifugation (Ausubel et al., supra) using a modified homogenization buffer (Chirgwin et al., *Biochemistry* 18:5294–5299 (1979)). Poly(A$^+$) RNA is selected by oligo(dT) chromatography (Aviv and Leder, *Proc Natl Acad Sci USA* 69:1408–1412 (1972)). RNA samples are stored at −80° C.

Analysis of gene expression and tissue distribution can be accomplished using Northern blots with, e.g., radiolabeled probes. The mRNA is size-separated using gel electrophoresis and then typically is transferred to a nylon membrane or to nitrocellulose and hybridized with radiolabeled probe. Presence of the hybridized probe is detected using autoradiography.

Cloning

The cDNA sequences encoding the opioid receptor protein are obtained from a random-primed, size-selected cDNA library.

Alternatively, the cDNA sequences encoding opioid receptor protein are obtained from a cDNA library prepared from mRNA isolated from cells expressing the receptor protein in various organs such as the brain, according to procedures described in Sambrook, J. et al., *MOLECULAR CLONING: A LABORATORY MANUAL*, 2nd Edition, Cold Spring Harbor Press, Cold Spring Harbor, N.Y., 1989.

The cDNA insert from the successful clone, excised with a restriction enzyme such as EcoRI, is then used as a probe of the original cDNA library or other libraries (low stringency) to obtain the additional clones containing inserts encoding other regions of the protein that together or alone span the entire sequence of nucleotides coding for the protein.

An additional procedure for obtaining cDNA sequences encoding the opioid receptor protein is PCR. PCR is used to amplify sequences from a pooled cDNA library of reversed-transcribed RNA, using oligonucleotide primers based on the transporter sequences already known.

Vector Construction

Construction of suitable vectors containing the desired coding and control sequences employs ligation and restriction techniques which are well understood in the art (Young et al., *Nature* 316:450–452 (1988)). Double-stranded cDNA encoding opioid receptor protein is synthesized and prepared for insertion into a plasmid vector CDM8. Alternatively, vectors such as Bluescript² or Lambda ZAP² (Stratagene, San Diego, Calif.) or a vector from Clontech (Palo Alto, Calif.) can be used in accordance with standard procedures (Sambrook, J. et al., supra).

Site specific DNA cleavage is performed by treating with the suitable restriction enzyme, such as EcoRI, or more than one enzyme, under conditions which are generally understood in the art, and the particulars of which are specified by the manufacturer of these commercially available restriction enzymes. See, e.g., New England Biolabs, Product Catalog. In general, about 1 μg of DNA is cleaved by one unit of enzyme in about 20 μl of buffer solution; in the examples herein, typically, an excess of restriction enzyme is used to ensure complete digestion of the DNA substrate. Incubation times of about one to two hours at about 37° C. are workable, although variations can be tolerated. After each incubation, protein is removed by extraction with phenol/chloroform, and can be followed by other extraction and the nucleic acid recovered from aqueous fractions by precipitation with ethanol.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of $Na^+$ and $Mg^{++}$ using about 1 unit of BAP or CIP per μg of vector at 60° C. or 37° C., respectively, for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

Ligations are performed in 15–50 μl volumes under the following standard conditions and temperatures: 20 mM Tris-HCl, pH 7.5, 10 mM $MgCl_2$, 10 mM DTT, 33 μg/ml BSA, 10 mM to 50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10–30 fold molar excess of linkers) are performed at 1 μM total ends concentration. Correct ligations for vector construction are confirmed according to the procedures of Young et al., *Nature*, 316:450–452 (1988).

cDNA Library Screening cDNA libraries can be screened using reduced stringency conditions as described by Ausubel et al., *CURRENT PROTOCOLS IN MOLECULAR BIOLOGY*, Greene Publishing and Wiley-Interscience, New York (1990), or by using methods described in Sambrook et al. supra), or by using a colony or plaque hybridization procedure with a fragment of the DOR-1 cDNA coding for opioid receptor protein.

Plaque hybridization is typically carried out as follows: Host bacteria such as LE 392 (Stratagene) are grown overnight at 37° in LB Broth (Sambrook et al., supra), gently pelleted and resuspended in one half the original volume of 10 mM $MgSO_4$, 10 mM $CaCl^2$. After titration, an amount of the phage library containing approximately 50,000 plaque forming units (pfu) is added to 300 μl of the host bacteria, incubated at 37° for 15 minutes and plated onto NZYCM agar with 10 ml NZYCM top agarose. A total of a million plaques distributed on twenty 15 cm plates are screened. For colony screening, transfected bacteria are plated onto LB broth plates with the appropriate antibiotics. After the plaques or colonies have grown to 1 mm, the plates are chilled at 4° C. for at least two hours, and then overlaid with duplicate nitrocellulose filters, followed by denaturation of the filters in 0.5 M NaOH/1.5 M NaCl for five minutes and neutralization in 0.5 M Tris, pH 7.4/1.5 M NaCl for five minutes. The filters are then dried in air, baked at 80° C. for two hours, washed in 5×SSC/0.5% SDS at 68° C. for several hours, and prehybridized in 0.5 M $NaPO_4$, pH 7.2/1% BSA/1 mM EDTA/7% SDS/100 μg/ml denatured salmon sperm DNA for more than 4 hours. Using the DOR-1 cDNA (described herein) labeled by random priming as a probe, high stringency hybridization is carried out in the same solution at 68° C., and the temperature is reduced to 50–60° C. for lower stringency hybridization. After hybridization for 16–24 hours, the filters are washed first in 40 mM $NaPO_4$, pH 7.2/0.5% BSA/5% SDS/1 mM EDTA twice for one hour each, then in 40 mM $NaPO_4$, pH 7.2/1% BSA/1 mM EDTA for one hour each, both at the same temperature as the hybridization (Boulton et al., *Cell* 65:663–675 (1991)). The filters are then exposed to film with an enhancing screen at −70° C. for one day to one week.

Positive signals are then aligned to the plates, and the corresponding positive phage is purified in subsequent rounds of screening, using the same conditions as in the primary screen. Purified phage clones are then used to prepare phage DNA for subcloning into a plasmid vector for sequence analysis. Tissue distribution of DNA corresponding to the various independent clones is analyzed using Northern blots and in situ hybridization using standard methods. Function of the DNA is tested using expression in a heterologous eucaryotic expression system such as COS cells.

Expression of Opioid Receptor Protein

The nucleotide sequence encoding opioid receptor protein can be expressed in a variety of systems. The cDNA can be excised by suitable restriction enzymes and ligated into procaryotic or eucaryotic expression vectors for such expression.

For example, as set forth below, the cDNA encoding the protein is expressed in COS cells. To effect functional expression, the plasmid expression vector CDM8 (Aruffo and Seed, *Proc Natl Acad Sci USA* 84:8573–8577 (1987), provided by Drs. Aruffo and Seed (Harvard University, Boston, Mass.) was used. Alternatively, other suitable expression vectors such as retroviral vectors can be used.

Procaryotic and prefereably eucaryotic systems can be used to express the opioid receptor. Eucaryotic microbes, such as yeast, can be used as hosts for mass production of the opioid receptor protein. Laboratory strains of *Saccharomyces cerevisiae*, Baker's yeast, are used most, although a number of other strains are commonly available. Vectors employing, for example, the 2 $\mu$ origin of replication (Broach, *Meth. Enz.* 101:307 (1983)), or other yeast compatible origins of replications (e.g., Stinchcomb et al., *Nature* 282:39 (1979)); Tschempe et al., *Gene* 10:157 (1980); and Clarke et al., *Meth. Enz.* 101:300 (1983)) can be used. Control sequences for yeast vectors include promoters for the synthesis of glycolytic enzymes (Hess et al., *J. Adv. Enzyme Reg.* 7:149 (1968); Holland et al., *Biochemistry* 17:4900 (1978)). Additional promoters known in the art include the promoter for 3-phosphoglycerate kinase (Hitzeman et al.,*J. Biol. Chem.* 255:2073 (1980)), and those for other glycolytic enzymes. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. It is also believed terminator sequences are desirable at the 3' end of the coding sequences. Such terminators are found in the 3' untranslated region following the coding sequences in yeast-derived genes.

Alternatively, genes encoding opioid receptor protein are expressed in eucaryotic host cell cultures derived from multicellular organisms. (See, e.g., *Tissues Cultures*, Academic Press, Cruz and Patterson, eds, (1973)). These systems have the additional advantage of the ability to splice out introns, and thus can be used directly to express genomic fragments. Useful host cell lines include amphibian cocytes such as Xenopus oocytes, COS cells, VERO and HeLa cells, Chinese hamster ovary (CHO) cells, and insect cells such as SF9 cells. Expression vectors for such cells ordinarily include promoters and control sequences compatible with mammalian cells such as, for example, the commonly used early and late promoters from baculovirus, vaccinia virus, Simian Virus 40 (SV40) (Fiers et al., *Nature* 273:113 (1973)), or other viral promoters such as those derived from polyoma, Adenovirus 2, bovine papilloma virus, or avian sarcoma viruses. The controllable promoter, hMTII (Karin et al., *Nature* 299:797–802 (1982)) may also be used. General aspects of mammalian cell host system transformations have been described by Axel, U.S. Pat. No. 4,399,216. It now appears, that "enhancer" regions are important in optimizing expression; these are, generally, sequences found upstream or downstream of the promoter region in non-coding DNA regions. Origins of replication can be obtained, if needed, from viral sources. However, integration into the chromosome is a common mechanism for DNA replication in eucaryotes.

If procaryotic systems are used, an intronless coding sequence should be used, along with suitable control sequences. The cDNA of opioid receptor protein can be excised using suitable restriction enzymes and ligated into procaryotic vectors along with suitable control sequences for such expression.

Procaryotes most frequently are represented by various strains of *E. coli*; however, other microbial species and strains may also be used. Commonly used procaryotic control sequences which are defined herein to include promoters for transcription initiation, optionally with an operator, along with ribosome binding site sequences, including such commonly used promoters as the β-lactamase (penicillinase) and lactose (lac) promoter systems (Chang et al., *Nature* 198:1056 (1977)) and the tryptophan (trp) promoter system (Goeddel et al., *Nucl Acids Res* 8:4057 (1980)) and the λ derived $P_L$ promoter and N-gene ribosome binding site (Shimatake et al., *Nature* 292:128 (1981)).

Depending on the host cell used, transformation is carried out using standard techniques appropriate to such cells. The treatment employing calcium chloride, as described by Cohen, *Proc Natl Acad Sci USA* (1972) 69:2110 (1972) or by Sambrook et al. (supra), can be used for procaryotes or other cells which contain substantial cell wall barriers. For mammalian cells without such cell walls, the calcium phosphate precipitation method of Graham and van der Eb, *Virology* 54:546 (1978), optionally as modified by Wigler et al., *Cell* 16:777–785 (1979), or by Chen and Okayama, supra, can be used. Transformations into yeast can be carried out according to the method of Van Solingen et al., *J. Bact.* 130:946 (1977), or of Hsiao et al., *Proc Natl Acad Sci USA* 76:3829 (1979).

Other representative transfection methods include viral transfection, DEAE-dextran mediated transfection techniques, lysozyme fusion or erythrocyte fusion, scraping, direct uptake, osmotic or sucrose shock, direct microinjection, indirect microinjection such as via erythrocyte-mediated techniques, and/or by subjecting host cells to electric currents. The above list of transfection techniques is not considered to be exhaustive, as other procedures for introducing genetic information into cells will no doubt be developed.

Modulation of Expression by Antisense Sequences

Alternatively, antisense sequences may be inserted into cells expressing opioid receptors as a means to modulate functional expression of the receptors encoded by sense oligonucleotides. The antisense sequences are prepared from known sense sequences (either DNA or RNA), by standard methods known in the art. Antisense sequences specific for the opioid receptor gene or RNA transcript can be used to bind to or inactivate the oligonucleotides encoding the opioid receptor.

Terminology

As used herein, the singular forms "a", "an" and "the" include plural reference unless the context clearly dictates otherwise. Thus, for example, reference to "a receptor" includes mixtures of such receptors, reference to "an opioid" includes a plurality of and/or mixtures of such opioids and reference to "the host cell" includes a plurality of such cells of the same or similar type and so forth.

Unless defined otherwise all technical and scientific terms used herein have the same meaning as commonly understood by one of ordinary skill in the art to which this invention belongs. The following examples are intended to illustrate but not to limit the invention. Temperatures are in ° C. and pressures at near atmospheric unless otherwise specified.

Preparation of Mono $^{125}$I-DADLE

DADLE (Peninsula Laboratories Inc.) was iodinated using the iodogen method (Maidment et al., in: *MICRODIALYSIS IN THE NEUROSCIENCES*, T. Robinson and J. Justice, eds., pp. 275–303 (Elsevier, 1991)). Both mono- and di-iodinated forms are produced. It has been reported that di-iodo-DADLE does not bind opiate receptors, due to the di-iodination of the tyrosine residue (Miller, R. J., et al., *Life Sci.* 22:379–88 (1978)). Accordingly, mono-iodinated DADLE is preferred. Mono-$^{125}$I-DADLE is also preferred because it has extremely high specific activity compared to DADLE labeled with other isotopes. Thus, exposure times on the order of days, rather than weeks or months can be used.

By employing a molar ratio of sodium iodide to peptide of approximately 1:100 when carrying out iodination, the yield of the preferred mono-iodinated DADLE was increased. Additionally, to further enhance the yield of the mono-iodinated form, iodinated DADLE (containing both mono- and di-iodinated forms) was purified by reverse-phase HPLC (Maidment et al., supra). Employing this procedure a single major radiolabeled peak of the mono-iodinated DADLE separated from di-iodinated and non-iodinated forms.

DADLE monolabeled with $^{125}$I is crucial to successful screening. Radiolabeled $^{125}$I-DADLE differs from DADLE in several important parameters: size, hydrophobicity, and binding affinity (slightly lower). The purification of mono-iodinated from di-iodinated and non-iodinated DADLE by the HPLC step yields a ligand with very high specific activity (approximately 2000 Ci/mmol). The specific activity of the mono-iodinated form is approximately 100 times greater than that obtained by using the unseparated mixture of mono-, di-, and non-iodinated DADLE. Monolabeled $^{125}$I-DADLE must be used within a few days of its preparation.

Example 1

Preparation of DOR-1

The NG108-15 cell line (available from Dr. Christopher Evans, UCLA) comprises a homogeneous and enriched source of delta opioid receptors. Utilizing mRNA isolated from NG108-15, a random-primed, size-selected cDNA library was constructed in plasmid vector CDM8. The cDNA library was amplified in bacteria. The cDNA library was transfected into COS-7 cells by electroporation. Transiently transfected COS lawns were screened and selected with highly purified mono-$^{125}$I-2dAla, 5dLeu enkephalin ($^{125}$I-DADLE). Positive clones were identified by film autoradiography, and plasmids from these cells were recovered and amplified in bacteria. Thereafter, the plasmids were re-transfected into COS cells. Following three cycles of such plasmid enrichment, individual clones were transfected and a pure clone was identified that bound $^{125}$I-DADLE.

A. Construction of the cDNA Library

RNA was prepared from NG108-15 cells by homogenization in 6 M guanidinium isothiocyanate, followed by centrifugation through cesium chloride (J. M. Chirgwin, et al., *Biochemistry* 18:5294 (1979)). Poly-A$^+$ RNA was isolated by chromatography over oligo-dT-cellulose (H. Aviv and P. Leder, *Proc Natl Acad Sci USA* 69:1408 (1972)). Using this RNA as a template, random hexamers were used to prime cDNA synthesis by avian myeloblastosis virus reverse transcriptase (Life Sciences Inc.). Second strand synthesis was accomplished with RNase-H and *E. coli* DNA polymerase (U. Gubler and B. J. Hoffman, *Gene* 24: 263 (1983)). The ends of the cDNAs were rendered blunt with T4 DNA polymerase and BstXI linkers were added. cDNA longer than 1.5 kb was selected by electrophoresis through 5% acrylamide followed by electro-elution. The 1.5 kb cDNA was ligated to the CDM8 vector (A. Aruffo and B. Seed, supra, and then transformed into MC-1061 bacteria by electroporation (W. J. Dower et al., *Nucl. Acids Res.* 16:6127 (1988)). Accordingly, six pools of plasmid DNA were prepared from the original cDNA library of approximately 2×10$^6$ recombinants.

B. Plasmid Transfection by Electroporation and Expression in COS cells

COS cells were grown at high density and were harvested in trypsin, then resuspended at 2×10$^7$/ml in 1.2× RPMI containing 20% fetal calf serum. These cells were then incubated for ten minutes at 4° C. with 20 μg recombinant plasmid DNA from the cDNA library described above, and then electroporated at 960 μF and 230 V in a 0.4 cm gap cuvette (BioRad). The cells were then incubated an additional ten minutes at 4° C., and then plated into Dulbecco's Modified Eagle's Medium (DMEM) plus 10 fetal calf serum (FCS).

C. Screening of Transfected COS Cells

The transfected COS cells as obtained above were grown for three days, then screened using radiolabeled mono $^{125}$I-DADLE. Transfected COS lawns were washed with PBS, then incubated at room temperature with 10–20 nM $^{125}$I-DADLE in KHRB containing 1% BSA. After 1 hour, the plates were washed rapidly several times with ice cold PBS then dried on ice with strong flow of forced cold air. Plates were exposed on Dupont Cronex film in cassettes at room temperature. Positive clones were identified by careful alignment of the film with the petri dish via low power microscopy.

DNA was removed from positive cells by solubilization in 0.1% SDS in TE containing 1 μg/μl tRNA delivered from a syringe attached to a capillary tube on a micromanipulator. Plasmids were purified from the extracted cells using the Hirt lysis procedure (Hirt, B., *J. Mol. viol.* 26:365–369 (1967)), and electroporated into MC-1061 bacteria. The plasmids were purified then retransfected into COS cells. Following three such enriching cycles, individual plasmid clones were transfected into COS cells yielding a single clone, named the DOR-1 clone.

Example 2

Characterization of DOR-1

The DOR-1 clone initially was characterized by screening cell membrane fractions, from cells expressing DOR-1, with the labelled DADLE it was found that binding of $^{125}$I DADLE was displaced by nanomolar concentrations of opiate alkaloids diprenorphine, morphine, etorphine, and by DADLE, DSLET and DPDPE. Dextrorphan (10 μM) did not displace the $^{125}$I DADLE, whereas its opioid-active enantiomer levorphanol did displace the radiolabeled DADLE. Additionally, the mu receptor-selective ligand DAGO (5 μM) did not displace the counts.

Figure 2:
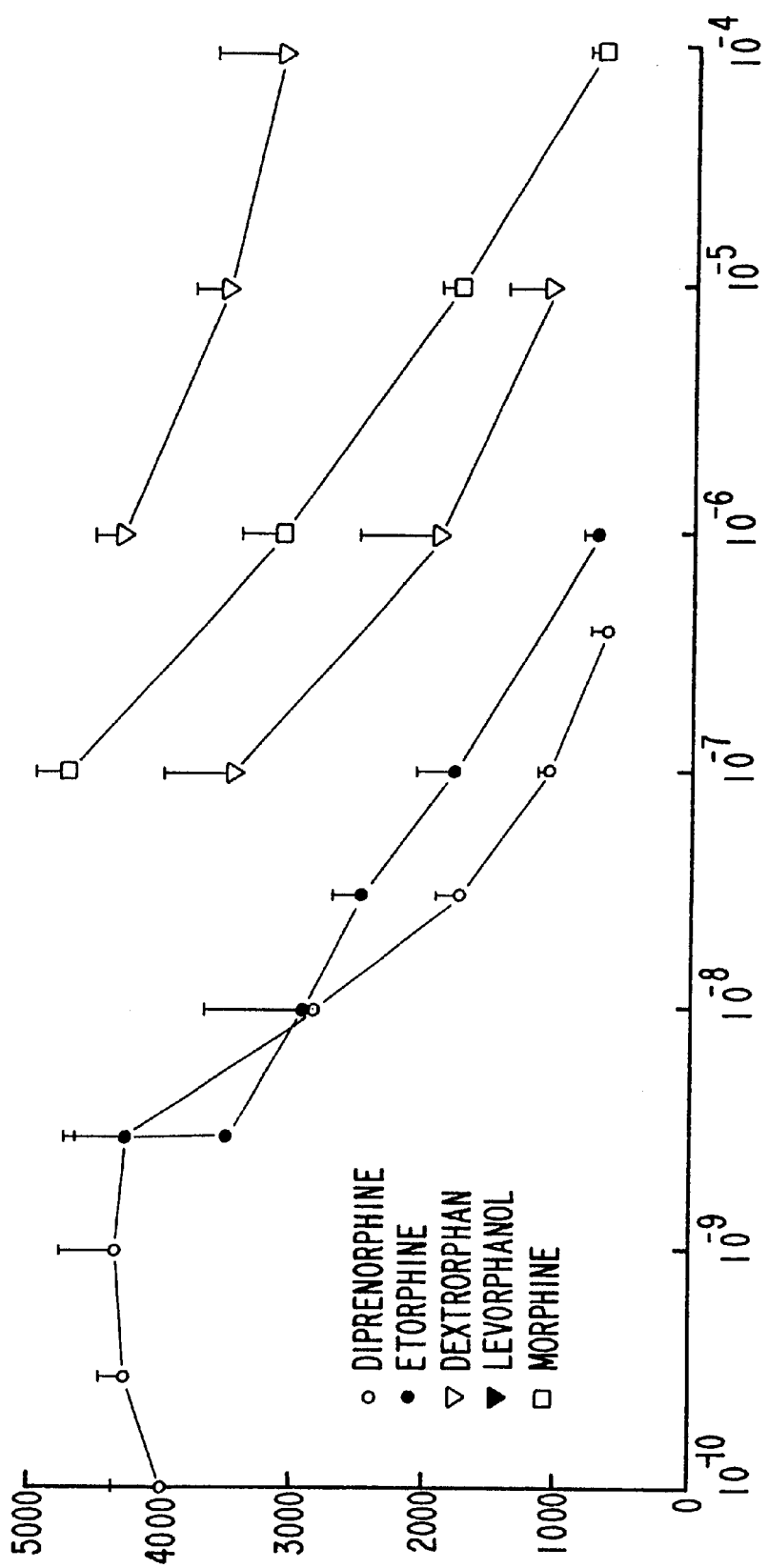
FIG. 2 depicts displacement curves of 5 nM $^3$H-diprenorphine from COS cell membranes of cells transfected with DOR-1. $^3$H-diprenorphine was displaced by diprenorphine, etorphine, morphine and levorphanol, but not by dextrorphan (the non-opiate active optical isomer of levorphanol).
Figure 3:
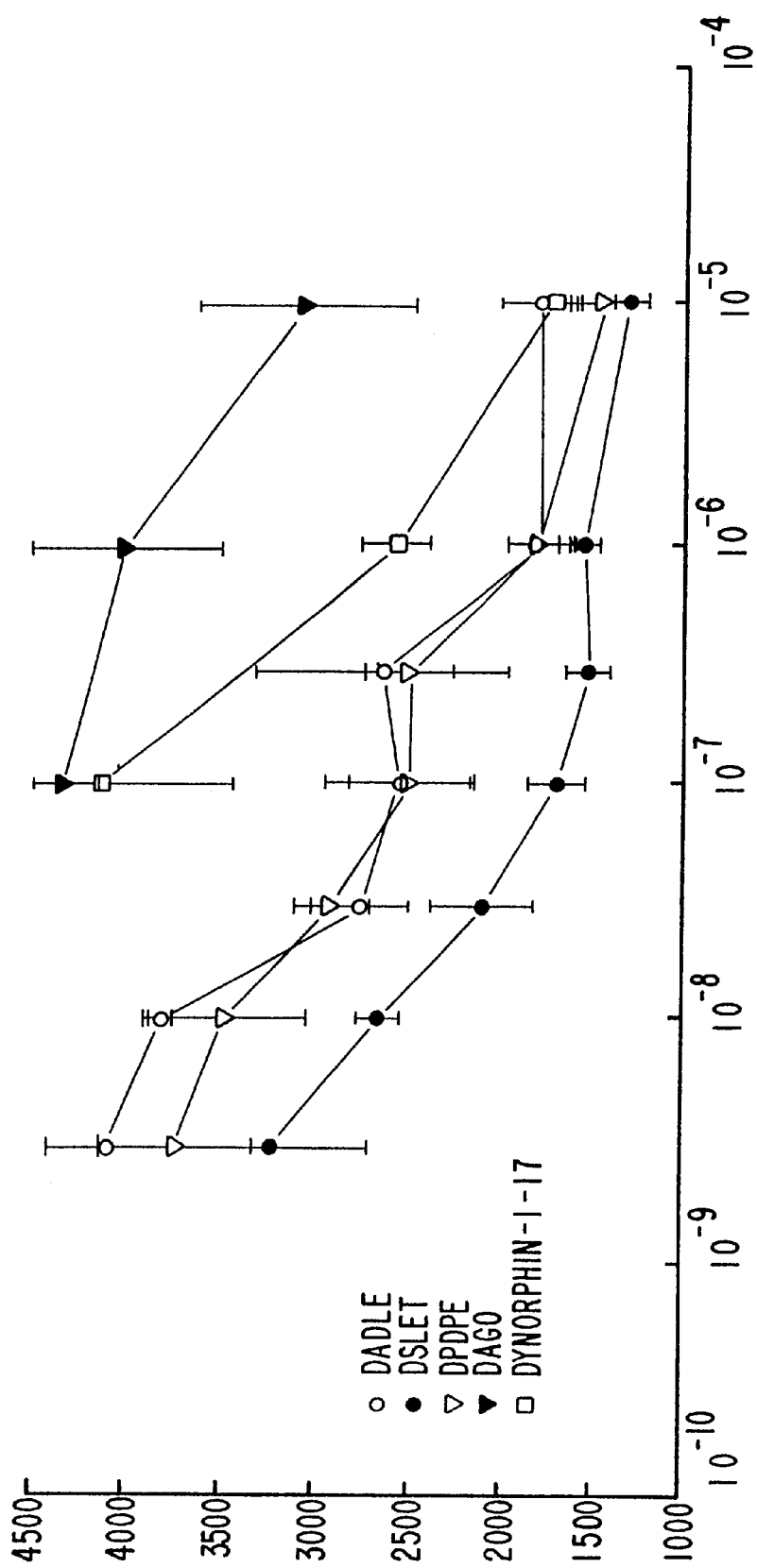
FIG. 3 depicts displacement curves of 5 nm $^3$H-diprenorphine from COS cell membranes of cells transfected with DOR-1. $^3$H-diprenorphine was displaced by DPDPE and DSLET, which are delta-selective agonists, by DADLE, a high affinity ligand for mu and delta receptors, and by dynorphin 1–17, a kappa-preferring ligand. $^3$H-diprenorphine was not displaced by DAGO, a mu-selective ligand.

The DOR-1 clone was further characterized pharmacologically by assessing binding of $^3$H-diprenorphine to intact cells expressing the DOR-1 clone (FIG. 1), and by assessing displacement of $^3$H-diprenorphine from membrane fractions of such cells (FIGS. 2 and 3).

Binding assays were conducted on intact cells in KRHB, 1% BSA; or on membranes in 25 mM HEPES, 5 mM MgCl$_2$ pH 7.7. Cells were harvested with PBS containing 1 mM EDTA, washed 2× with PBS then resuspended in KHRB. Membranes prepared from the cells (Law P. Y. E et al., *Mol. Pharm.* 23:26–35 (1983)) were used directly in the binding assay. Binding assays were conducted in 96 well polypropylene cluster plates (Costar), at 4° C. in a total volume of 100 μl with an appropriate amount of radiolabeled ligand. Following 1 hour of incubation, plates were harvested on a Tomtec harvester and "B" type filtermats were counted in a Betaplate (Pharmacia) scintillation counter using Meltilex B/HS (Pharmacia) melt-on scintillator sheets.

Intact cells expressing DOR-1 were analyzed with the high affinity opiate antagonist $^3$H-diprenorphine. Specific binding was defined by the counts displaced by 400 nM diprenorphine. FIG. 1 shows a saturation curve for $^3$H-diprenorphine for NG108-15 cells, and COS-7 cells transfected with the delta opioid receptor clone. Untransfected COS cells, or COS cells transfected with plasmid having no insert showed no specific binding. Thus, the opioid binding of COS-DOR-1 cells was similar to that of NG108-15 cells.

Membranes prepared by standard methods from transfected COS-7 cells were employed for a more extensive pharmacological characterization of the receptor encoded by the DOR-1 clone. The affinities for the following alkaloid opiates in competition for $^3$H-diprenorphine are illustrated in FIG. 2: unlabeled diprenorphine, a high affinity antagonist for delta receptors; etorphine, a high affinity agonist for delta, mu and kappa receptors; levorphanol, a low affinity agonist for delta receptors; morphine, a low affinity agonist for delta receptors and a high affinity agonist for mu receptors; and dextrorphan, a non-opiate active enantiomer of levorphanol which should not bind delta receptors.

As shown in FIG. 2, the displacement of $^3$H-diprenorphine, in decreasing order of affinity, was observed with diprenorphine, etorphine, levorphanol and morphine. As expected, $^3$H-diprenorphine was not displaced by dextrorphan.

The affinities of the following opioid peptides in competition for $^3$H-diprenorphine are set forth in FIG. 3: DADLE, a high affinity agonist for mu and delta receptors; DSLET and DPDPE, both high affinity agonists of delta (but not mu) receptors; DAGO, a selective agonist for mu receptors; and Dynorphin 1–17, a high affinity agonist for kappa receptors and moderate to low affinity agonist for delta receptors. As shown in FIG. 3, the displacement of $^3$H-diprenorphine, in decreasing order of affinity, was observed for DSLET, DPDPE and DADLE, and Dynorphin 1–17. Only weak displacement by DAGO was observed.

Example 3
Northern Blot Analysis of RNA

For Northern analysis, the mRNA from NG108-15 cells, and from cells dissected from regions of rat brain was separated by electrophoresis through 2.2 M formaldehyde/1.5% agarose, blotted to nylon and hybridized in aqueous solution at high stringency. The filters were prehybridized in 0.5 M NaPO$_4$, pH 7.2; 1% BSA; 1 mM EDTA; 7% SDS; and 100 μg/ml denatured salmon sperm DNA for at least four hours at 68° C. (Boulton et al., supra). The filters were then hybridized overnight under these same conditions with a ≧5×10$^6$ cpm/ml purified cDNA insert labelled by random priming (A. P. Feinberg and B. Vogelstein, Anal. Biochem. 132:6 (1983)). The filters were twice washed in 40 mM NaPO$_4$, pH 7.2; 0.5% BSA; 5% SDS; and 1 mM EDTA for one hour, and then washed twice in 40 mM NaPO$_4$, pH 7.2; 1% SDS; and 1 mM EDTA for one hour each, all at 68° C. Thereafter autoradiography was performed with DuPont Cromex Lightening Plus at −70° C.

Figure 4:
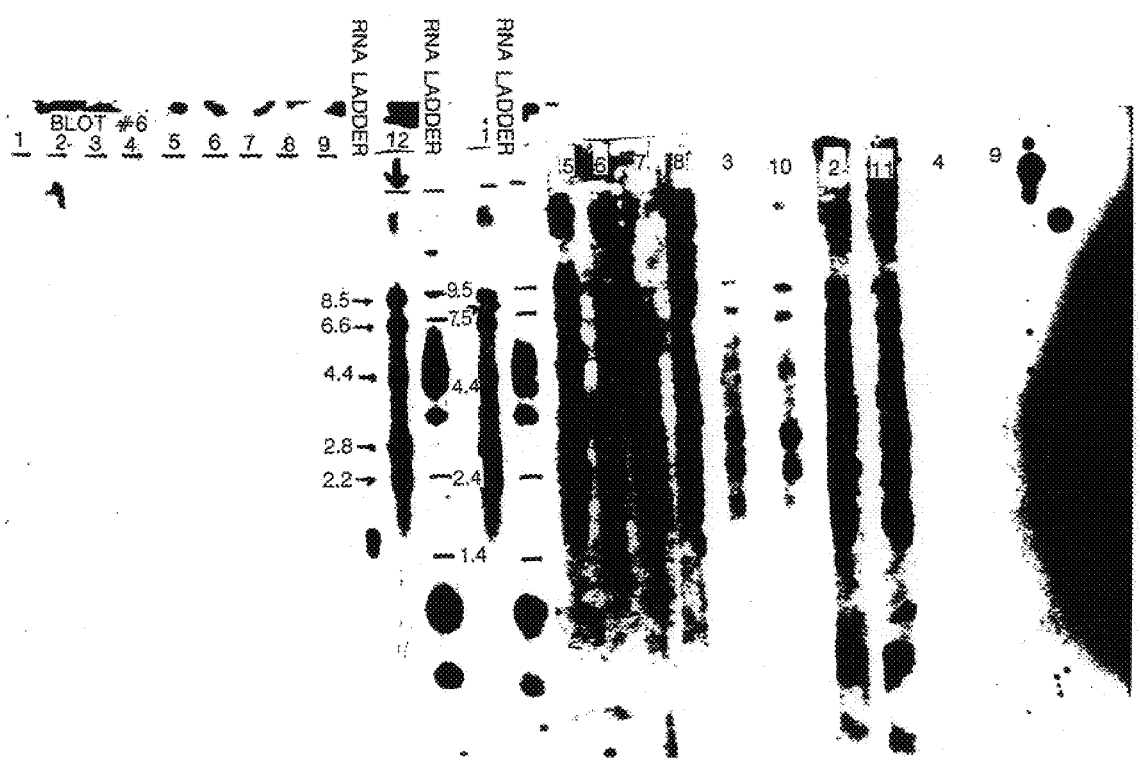
FIG. 4 depicts the results of a Northern analysis of mRNA from NG108-15 cells and cells from various rat brain regions.

The results of the Northern analysis of the mRNA showed the presence of multiple bands hybridizing to the probe at approximately 8.7, 6.8, 4.4, 2.75 and 2.2 kilobases (Kb) (FIG. 4). Also, the Northern analysis indicates that the pattern of mRNA may vary between brain regions. At present, it is unclear whether these mRNAs encode different protein sequences, and if so, whether these messages represent different types or sub-types of opioid receptors.

Example 4
Southern Blot Analysis of DNA

Figure 7:
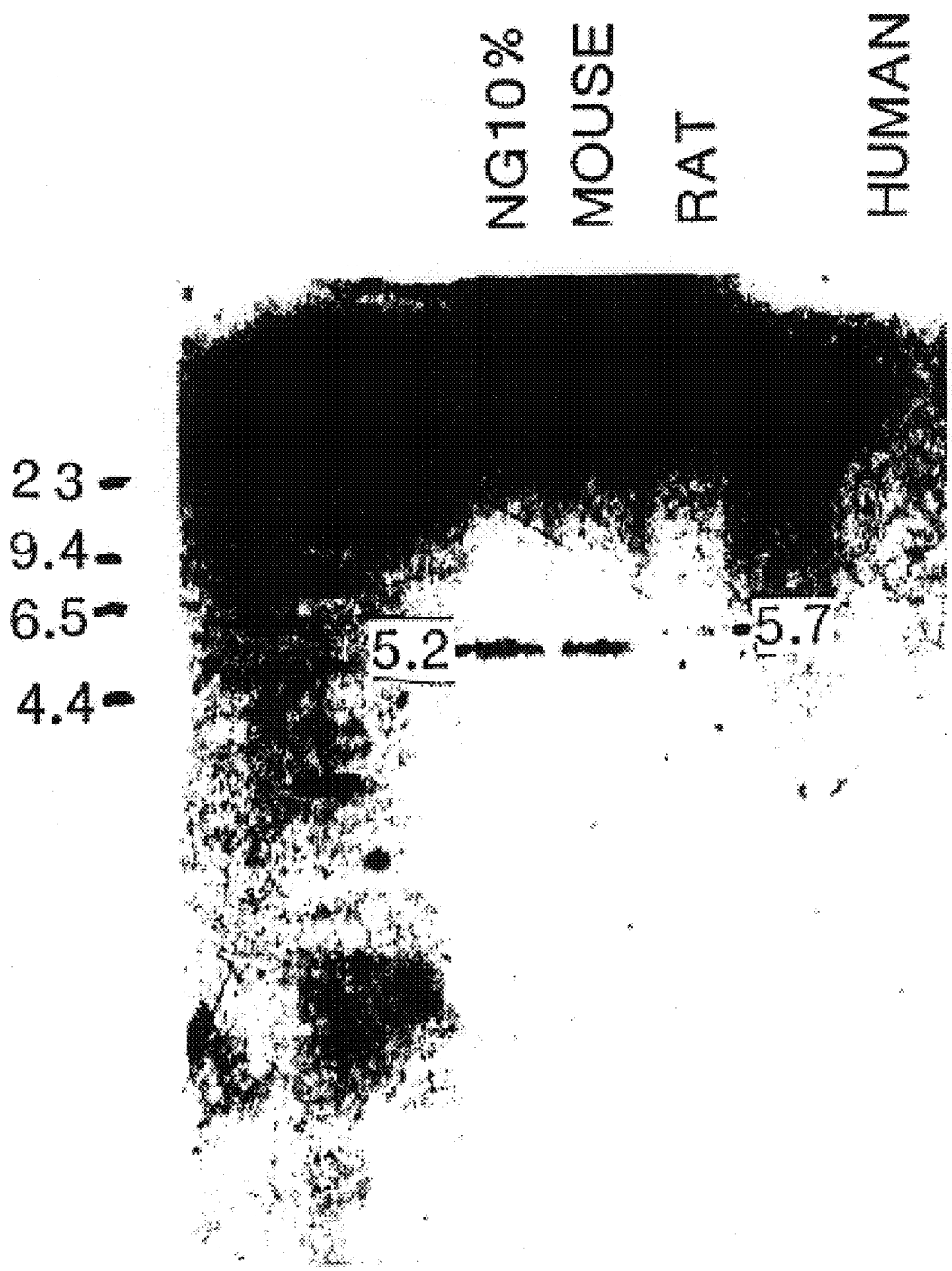
FIG. 7 depicts a Southern blot of radiolabeled DOR-1 cDNA probe hybridized at high stringency to NG108-15, mouse, rat and human DNA cut with BamHI.

The radiolabeled DOR-1 cDNA probe was hybridized to genomic Southern blots by standard methods (Sambrook et al., supra). Accordingly, the radiolabeled DOR-1 cDNA probe was hybridized under high stringency conditions to a blot of NG108-15, mouse, rat and human DNA cut with restriction endonuclease BamHI (FIG. 7). Single bands were observed in the clones containing the NG108-15, mouse, and rat DNA. The sizes of the bands hybridizing to the cDNA probe were estimated to be 5.2 kb (NG108-15), 5.2 kb (mouse), and 5.7 kb (rat). These results indicate the close homology of the mouse and rat genes, and also demonstrate that the DOR-1 clone is from the murine parent of the NG108-15 cell line.

In a blot containing EcoRI-cut genomic DNA from many different species, hybridization of the DOR-1 cDNA under conditions of moderate stringency showed two bands in each lane of mouse, rat, human, rabbit, and several other mammalian species. This demonstrates a close relationship between opioid receptor genes in all of these species. Further, these results show that the genes or cDNAs from each of these species may readily be cloned using hybridization under moderate stringency.

Example 5
Determination of the cDNA Sequence

Isolated cDNA represented by the DOR clone was analyzed by subcloning the insert from the cDNA clone into a plasmid such as pBluescript™ (Stratagene, San Diego, Calif.) and using the dideoxy method (Sanger et al., Proc Natl Acad Sci USA 74:5463–5467 (1977)). The sequence of the cDNA was determined from single-stranded EDNA and specifically designed internal primers, using both Sequenase and ΔTaq cycle sequencing kits (USB). These kits, widely used in the art, utilize the dideoxy chain termination method. The DNA sequence and predicted protein sequence was then compared to sequences in established databanks such as GenBank.

Sequencing the cDNA insert in the DOR-1 clone, revealed an open reading frame of 370 amino acids (FIG. 5). Comparisons with known sequences in GenBank showed highest homology between DOR-1 and the G-protein-coupled somatostatin receptor (57% amino acid identity), and slightly lower homology with the receptors binding angiotensin, the two chemotactic factors IL-8 and N-formyl peptide. FIG. 6 shows the homology to the human somatostatin 1 receptor. The close homology of the present receptor clone with the somatostatin receptor is especially noteworthy since somatostatin ligands are reported to bind to opioid receptors, and to have molecular mechanisms similar to those in delta receptors.

Other features of the DOR-1 clone amino acid sequence deduced from the cDNA sequence include three consensus glycosylation sites at residues 18 and 33 (predicted to be in the extracellular N-terminal domain), and at residue 310 (close to the C-terminus and predicted to be intracellular). Phosphokinase C consensus sites are present within predicted intracellular domains, at residues 242, 255, 344, and 352. Seven putative membrane-spanning regions were identified based on hydrophobicity profiles, as well as homology with Rhodopsin and other G-protein coupled receptors which have been analyzed with respect to membrane-spanning regions using MacVector (I.B.I.) analysis. The DOR-1 clone isolated in accordance with the principles of the present invention produces a delta receptor with a predicted molecular weight of 40,558 daltons prior to post-translational modifications such as N-glycosylation.

Example 6

Isolation of Opioid Receptor Genomic Clones

Isolation of genomic clones was carried out according to techniques known in the art. To isolate opiate receptor genomic clones, 300,000 human genomic clones in γgem 11 (Promega) and a similar number of mouse genomic clones in lambda Fix (Stratagene) were plated on host strain Le392 and probed with the 1.1 kb DOR-1 Pst/Xba I fragment, which contains primarily the coding region. The conditions for hybridization were of fairly low stringency: 50% formamide/6×SSC, overnight at 37° C. The washes were performed also at low stringency: 2×SSC, 0.1 SDS at room temperature.

One mouse clone and three human genomic clones were isolated and purified by sequential rounds of hybridization and plaque purification. DNA preparation and restriction analysis showed that the three human clones had very different EcoRI digestion patterns. The 1.1 kb opiate receptor probe hybridized to a different single EcoRI band in Southern blot analysis for each clone. These results indicated preliminarily that three different genes were represented by the human genomic clones which were designated H3, H14 and H20 (see FIGS. 8a, 8b, 8c and 8d). Each of these clones was deposited on Aug. 13, 1993 at the American Type Culture Collection, Rockville, Md., under conditions of the Budapest Treaty. All restrictions on access to these deposits will be irrevocably removed at the time a patent issues in the United States on the basis of this application. The ATCC deposit numbers are 75549 for H20; 75550 for H14 and 75551 for H3.

The H3, H14 and H20 clones were digested into smaller fragments by EcoRI and TaqI and then shotgun cloned into the appropriate site of Bluescript for sequencing. The partial nucleotide sequence for H3 is shown in FIG. 8a; the partial nucleotide sequence of H14 is shown in FIG. 8b; the partial nucleotide sequence of H20 is shown in FIG. 8c.

The three genomic clones were mapped by in situ hybridization on human metaphase chromosomes by Dr. Glenn Evans of the Salk Institute. H3 maps to chromosome 1P; H14 maps near the centromere of chromosome 8, and H20 maps to chromosome 6. Comparison of sequence data obtained as described above with the published sequences for the murine counterparts referenced hereinabove, and with the DOR-2 clone described hereinbelow, confirmed that: (a) H3 encodes the human delta opioid receptor; (b) H14 encodes the human kappa opioid receptor and (c) H20 encodes the human mu receptor. In addition, H20 appears to contain a CACACA marker (FIG. 8d) which provides a means to track the inheritance of this gene.

The genomic clones were digested into smaller fragments by EcoRI and TaqI, then shotgun cloned into the appropriate site of Bluescript for sequencing.

Example 7

Isolation of Opioid Receptor Clones From Additional Organisms

In order to isolate the opioid receptor from mammalian brain cells, for example human brain cells, a random-primed human brainstem cDNA library in λ Zap (Stratagene) was screened using the murine cDNA encoding the DOR-1 described herein. Positive plaques were purified and rescreened. Individual positive clones are sequenced and characterized as above.

Example 8

Determination of Probable Antigenic Sequences

By evaluating the amino acid sequence of the opioid receptor encoded by DOR-1 with the MacVector (I.B.I.) antigenic index, and the antigenic index in accordance to Jameson, B. and H. Wolf, Comput. Applic. in Biosci. 4:181–186 (1988), the following underlined sequences of the delta opioid receptor were determined to have a high antigenic potential:

$NH_2$
MELVPSARAELOSSPLVNLSDAFPSAFPSAGANA-
SGSPGARSA SSLALAIAITALYSAVCAVGLLGNV-
LVMFGIVRYTKLKTATNIYI FNLALADALAT-
STLPFQSAKYLMETWPFGELLCKAVLSI-
DYYNMF TSIFTLTMMSVDRYIAV
CHPVKALDFRTPAKAKLINICIWVLASG
VGVPIMVMAVTQPRDGAVVCMLQF-
PSPSWYWDTVTKICVFLFAFV VPILIITVCYGLM-
LLRLRSVRLLSGSKEKDRSLRRITRMVLVVVG
AFVVCWAPIHIFVIVWTLVDINRRDPLV-
VAALHLCIALGYANSSL NPVLYAFLDENFKRC-
FRQLCRTPCGROEPGSLRRPROATTRERVT A
CTPSDGPGGGAAA-COOH (SEQ ID NO:2).

The N-terminal sequence is extracellular, the other four sequences are predicted to be intracellular.

Example 9

Recovery of the Murine Clone DOR-2 (mMOR-1)

A cDNA library prepared from mouse brain in λgt10 was probed using the low-stringency conditions of Example 6 using DOR-1 as a probe. One clone was recovered, inserted into Bluescript and sequenced. Northern and Southern blots indicated divergence from DOR-1. This clone, designated DOR-2, represented a new gene. DOR-2 hybridized to a different pattern of neurons than did DOR-1 and showed greater labeling of the striatum. Expression of DOR-1 by insertion into the vector pCDNA and transfection into mammalian cells produced cells which bind morphine, indicative of a mu-receptor. The cells also bind the nonselective opiate antagonist diprenorphine. The identity of DOR-2 (mMOR-1) as that of a mu receptor was confirmed by the displacement of $^3$H-DPN by nanomolar concentrations of the mu-selective ligands morphiceptin, DAMGO and morphine. The delta selective ligands DPDPE and deltorphan did not displace the binding and naloxone had the expected high affinity. The partial sequence designated H20, described in Example 6, was substantially similar to DOR-2. The partial sequence of DOR-2 is shown in FIG. 9.

FIG. 10 shows a comparison of the amino acid sequences of murine delta receptin with the rat mu and kappa receptors. There are extensive regions of homology.

What is claimed is:

1. A nucleic acid probe that hybridizes to the complement of SEQ ID NO:12 under high stringency conditions, wherein said high stringency conditions are defined as washing twice in 40 mM NaPO$_4$, pH 7.2; 0.5% BSA; 5% SDS; and 1 mM EDTA for one hour at 68° C. followed by washing twice in 40 mM NaPO$_4$, pH 7.2; 1% SDS; and 1 mM EDTA for one hour at 68° C. and specifically identifies a mammalian kappa opioid receptor clone in a cDNA library.

2. A nucleic acid probe that hybridizes under high stringency conditions to the complement of SEQ ID NO:13 or 15, wherein said high stringency conditions are defined as washing twice in 40 mM NaPO$_4$, pH 7.2; 0.5% BSA; 5% SDS; and 1 mM EDTA for one hour at 68° C. followed by washing twice in 40 mM NaPO$_4$, pH 7.2; 1% SDS; and 1 mM EDTA for one hour at 68° C. and specifically identifies a mammalian mu opioid receptor clone in a cDNA library.

3. An isolated and purified or recombinant DNA molecule containing a nucleotide sequence encoding a mammalian kappa opioid receptor which nucleotide sequence hybridizes under conditions of high stringency, wherein said high stringency conditions are defined as washing twice in 40 mM NaPO$_4$, pH 7.2; 0.5% BSA; 5% SDS; and 1 mM EDTA for one hour at 68° C. followed by washing twice in 40 mM NaPO$_4$, pH 7.2; 1% SDS; and 1 mM EDTA for one hour at 68° C., to a probe consisting of the nucleotide sequence SEQ ID NO: 12 or to its complement.

4. A DNA molecule comprising an expression system which, when transformed into a host, produces a mnammalian kappa opioid receptor in the host, which expression system comprises a nucleotide sequence encoding said opioid receptor operably linked to heterologous control sequences operable to effect expression of said nucleotide sequence in said host, wherein said opioid receptor is defined as encoded by a nucleotide sequence which hybridizes under conditions of high stringency to the nucleotide sequence SEQ ID NO: 12 or to its complement, wherein said high stringency conditions are defined as washing twice in 40 mM NaPO$_4$, pH 7.2; 0.5% BSA; 5% SDS; and 1 mM EDTA for one hour at 68° C. followed by washing twice in 40 mM NaPOa$_4$, pH 7.2; 1% SDS; and 1 mM EDTA for one hour at 68° C.

5. Recombinant host cells modified to contain the expression system of claim 4.

6. A method to produce recombinant cells that display mammalian kappa opioid receptors at their surface, which method comprises culturing the cells of claim 5 under conditions that effect expression of the encoding nucleotide sequence to produce said receptors at their surface.

7. An isolated ad purified or recombinant DNA molecule containing a nucleotide sequence encoding a mammalian mu opioid receptor which nucleotide sequence hybridizes under conditions of high stringency, wherein said high stringency conditions are define as washing twice in 40 mM NaPO$_4$, pH 7.2; 0.5% BSA; 5% SDS; and 1 mM EDTA for one hour at 68° C. followed by washing twice in 40 mM NaPO$^4$, pH 7.2; 1% SDS; and 1 mM EDTA for one hour at 68° C., to a probe consisting of the nucleotide sequence SEQ ID NO: 13 or 15 or to its complement.

8. A DNA molecule comprising an expression system which, when transformred into a host, produces a mammalian mu opioid receptor in the host, which expression system comprises a nucleotide sequence encoding said opioid receptor operably linked to heterologous control sequences operable to effect expression of said nucleotide sequence in said host, wherein said opioid receptor is defined as encoded by a nucleotide sequence which hybridizes under conditions of high stringency to the nucleotide sequence SEQ ID NO: 13 or 15 or to its complement, wherein said high stringency conditions are defined as washing twice in 40 mM NaPO$_4$, pH 7.2; 0.5% BSA; 5% SDS; and 1 mM EDTA for one hour at 68° C. followed by washing twice in 40 mM NaPO$_4$, pH 7.2; 1% SDS; and 1 mM EDTA for one hour at 68° C.

9. Recombinant host cells modified to contain the expression system of claim 8.

10. A method to produce recornbinant cells that display mammalian mu opioid receptors at their surface, which method comprises culturing the cells of claim 9 under conditions that effect expression of the encoding nucleotide sequence to produce said receptors at their surface.

\* \* \* \* \*